(12) United States Patent
White et al.

(10) Patent No.: US 8,212,563 B2
(45) Date of Patent: *Jul. 3, 2012

(54) METHOD AND APPARATUS FOR IN-SITU MEASUREMENT OF SOOT BY ELECTRON SPIN RESONANCE (ESR) SPECTROMETRY

(75) Inventors: James Robert White, San Bruno, CA (US); Christopher John White, Palo Alto, CA (US); Colin T. Elliott, San Francisco, CA (US); Alexander H. Slocum, Bow, NH (US)

(73) Assignee: Active Spectrum, Inc., Foster City, CA (US)

( * ) Notice: Subject to any disclaimer, the term of this patent is extended or adjusted under 35 U.S.C. 154(b) by 494 days.

This patent is subject to a terminal disclaimer.

(21) Appl. No.: 12/387,766

(22) Filed: May 6, 2009

(65) Prior Publication Data

US 2009/0230962 A1 Sep. 17, 2009

Related U.S. Application Data

(63) Continuation-in-part of application No. 11/983,393, filed on Nov. 8, 2007, now Pat. No. 7,868,616, and a continuation-in-part of application No. 11/590,522, filed on Oct. 31, 2006, now Pat. No. 7,589,529.

(60) Provisional application No. 61/050,989, filed on May 6, 2008.

(51) Int. Cl.
*G01V 3/00* (2006.01)
(52) U.S. Cl. ........................................ 324/316; 324/318
(58) Field of Classification Search .......... 324/300–322; 600/407–435; 382/128–131
See application file for complete search history.

(56) References Cited

U.S. PATENT DOCUMENTS

| 3,140,993 A | | 7/1964 | Roberts |
| 3,701,959 A | * | 10/1972 | Hansen .................. 333/227 |
| 4,360,776 A | | 11/1982 | Bauman |
| 4,593,248 A | | 6/1986 | Hyde et al. |

(Continued)

FOREIGN PATENT DOCUMENTS

DE 198 34 939 2/2000

(Continued)

OTHER PUBLICATIONS

PCT International Search Report and the Written Opinion of the International Searching Authority for PCT/IB2006/003174.

(Continued)

*Primary Examiner* — Louis Arana
(74) *Attorney, Agent, or Firm* — Tope-McKay & Associates; Autumn Villarreal

(57) ABSTRACT

An instrument and method using electron spin resonance spectrometry for measuring the concentration of airborne soot particles, and the like, that includes continuously passing a sample of exhaust gas through a resonating RF microwave cavity resonator during the application therethrough of a uniform slowly varying uniform magnetic field that is rapidly modulated and measuring the resulting phase modulation or amplitude modulation thereof to derive an electron spin resonance signal that directly senses the concentration of carbon free radicals produced as a result of inefficient combustion of hydrocarbons during operation of the vehicle or boiler. A further invention is the use of this signal for feedback control of the engine or boiler operating parameters to minimize or substantially eliminate particulate matter emissions.

16 Claims, 16 Drawing Sheets

U.S. PATENT DOCUMENTS

| | | | |
|---|---|---|---|
| 5,233,303 | A | 8/1993 | Bales et al. |
| 5,294,885 | A * | 3/1994 | Gentsch et al. ............... 324/316 |
| 6,268,727 | B1 * | 7/2001 | King et al. .................... 324/306 |
| 7,260,930 | B2 | 8/2007 | Decou et al. |
| 7,589,529 | B1 * | 9/2009 | White et al. .................. 324/316 |
| 7,868,616 | B2 * | 1/2011 | White et al. .................. 324/316 |
| 2003/0155916 | A1 | 8/2003 | Maier et al. |
| 2007/0024289 | A1 | 2/2007 | Knitt et al. |

FOREIGN PATENT DOCUMENTS

| | | |
|---|---|---|
| JP | 2002 062271 | 2/2002 |

OTHER PUBLICATIONS

Chzhan, M., et al., "A Tunable Reentrant Resonator with Transverse Orientation of Electric Field forin VivoEPR Spectroscopy," Journal of Magnetic Resonance, Academic Press, Orlado, FL, US, vol. 137, No. 2, Apr. 1, 1999, pp. 373-378.

White, J., "Micro-ESR for Airborne Soot Measurement," 2008 Diesel Engine-Efficiency and Emissions Research (DEER) Conference Presentations, [online] Aug. 4, 2008, Dearborn, Michigan, Retrieved from the Internet: http://www1.eere.energy.gov/vehiclesandfuels/resources/proceedings/2008_deer_presentations.html [retrieved Nov. 25, 2008].

J. R. White, et al., "Octave-Tunable Miniature RF Resonators," IEEE Microwave and Wireless Components Letters, Vo. 15, No. 11, Nov. 2005.

* cited by examiner

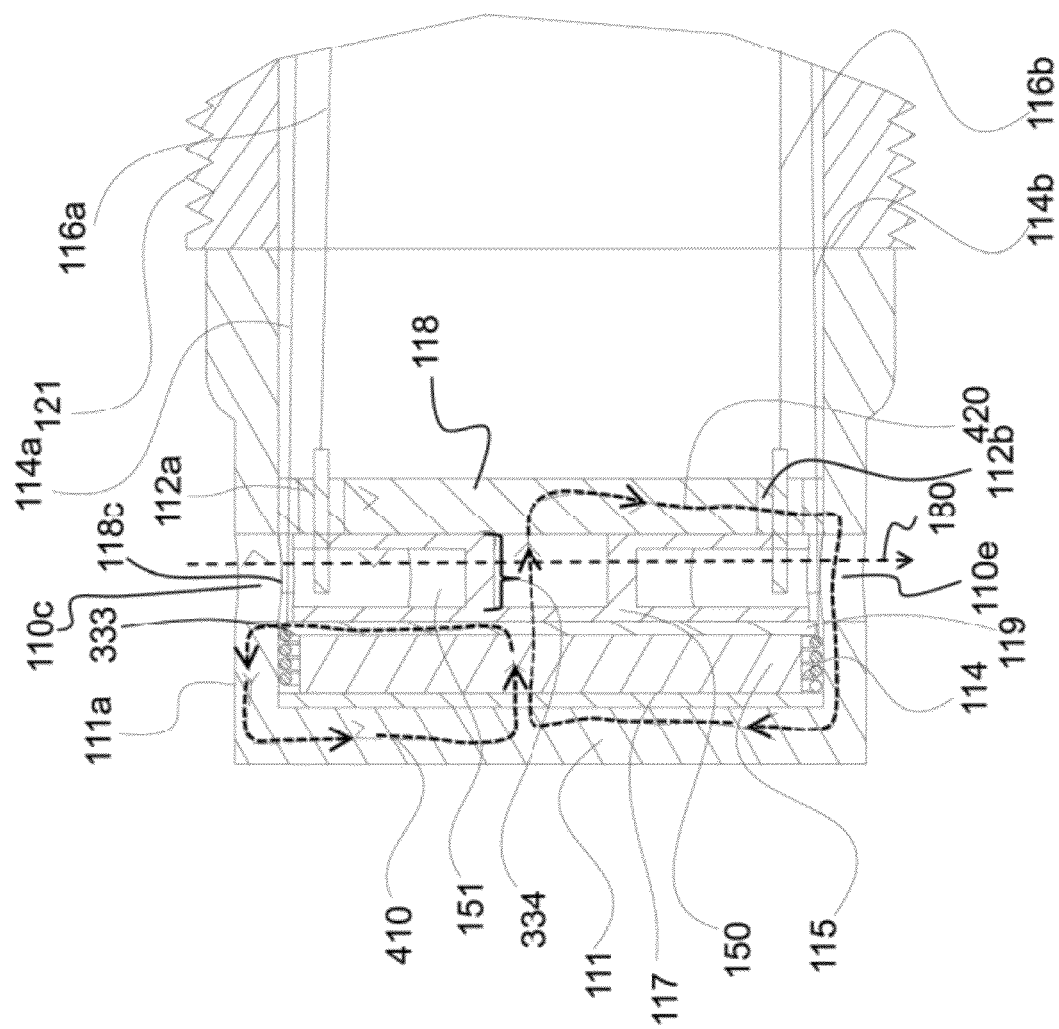

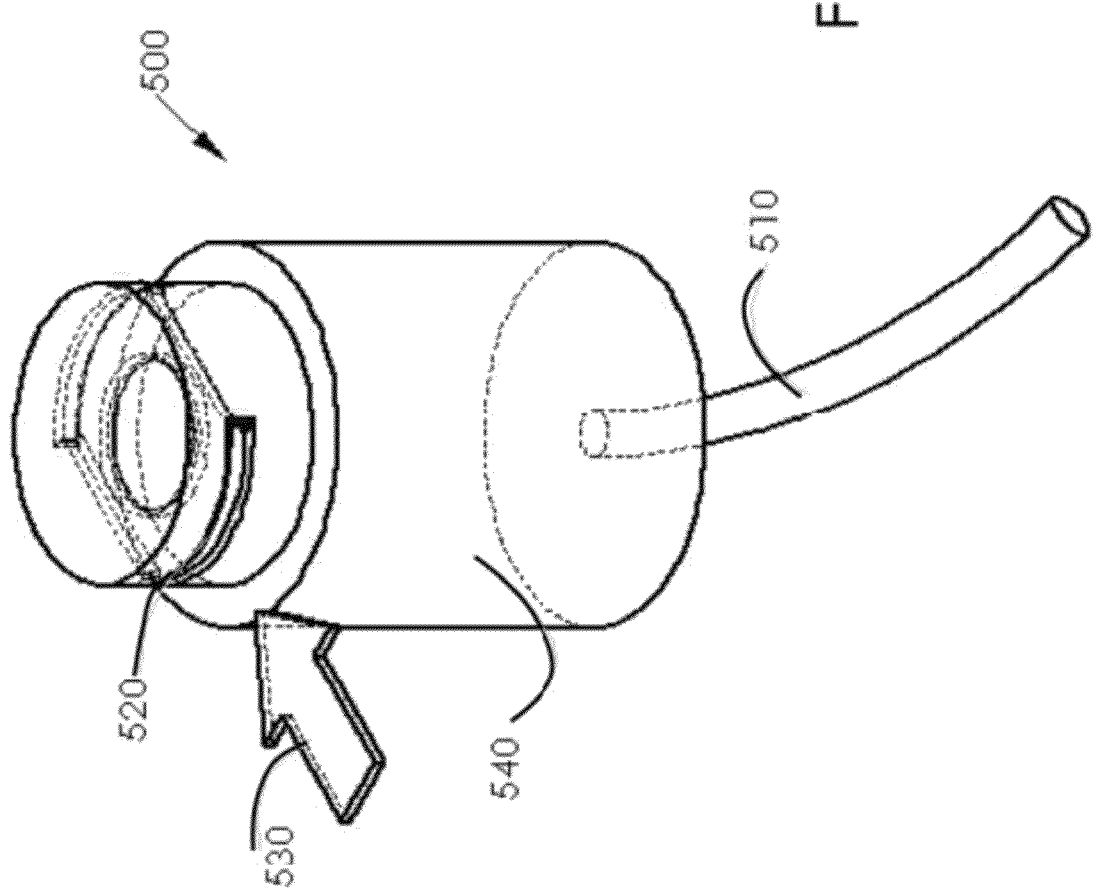

METHOD AND APPARATUS FOR IN-SITU MEASUREMENT OF SOOT BY ELECTRON SPIN RESONANCE (ESR) SPECTROMETRY

PRIORITY CLAIM

The present application is a Continuation-in-Part application of U.S. application Ser. No. 11/983,393, filed Nov. 8, 2007, entitled, "Method of And Apparatus for In-Situ Measurement of Changes in Fluid Composition By Electron Spin Resonance (ESR) Spectrometry," and U.S. application Ser. No. 11/590,522, filed Oct. 31, 2006, entitled, "Method Of And Apparatus For In-Situ Measurement of Degradation of Automotive Fluids And The Like By Micro-Electron Spin Resonance (ESR) Spectrometry." The present application is also a Non-Provisional Utility application of U.S. Provisional Application No. 61/050,989, filed on May 6, 2008, and entitled, "Method of and Apparatus for In-Situ Measurement of Soot by Electron Spin Resonance (ESR) Spectrometry."

FIELD OF THE INVENTION

The invention relates to the field of electron spin resonance (ESR) spectrometry and, more particularly, to the use of such technology for sensing the real-time, in situ emissions of soot particulates in the exhaust of operating machinery, and to a system for using the soot sensor for feedback control of the operating parameters to reduce or substantially eliminate soot emissions.

BACKGROUND OF THE INVENTION

The monitoring of soot generated by combustion processes in machinery, in vehicles, generators, engines, boilers, and the like (all hereinafter, for convenience, generically referred to as "machinery") is vital to ensuring compliance with environmental regulations on particulate matter (PM) emissions. In the United States, the environmental protection agency (EPA) has mandated reductions in particulate matter emissions from diesel engines, referred to as PM10 and PM2.5 (which refers to fine particles less than 10 microns and 2.5 microns in size, respectively.) Inhalation of fine particles is associated with serious health effects, and pollution such as smog. There is no single sensor available that can adequately monitor soot in-situ, as prior art technology is subject to fouling, susceptible to vibrations, insufficiently sensitive, or non-specific. Prior art soot sensor technology includes U.S. patent application Ser. No. 11/770,396 filed Jun. 28, 2007, which discloses a soot sensor representing the image charge method of measurement. The sensor design is similar to a spark plug. Soot particles in the exhaust, a fraction of which are charged, reduce the breakdown voltage of the spark gap. A second type of soot sensor is disclosed in U.S. patent application Ser. No. 11/827,029, filed Jul. 10. 2007. This method measures the mass of soot accumulated on a quartz microbalance placed in the exhaust stream. A resistive heater is manufactured on top of the resonant element to oxidize accumulated soot. Microbalances respond to any material or liquid absorbed on the surface of the resonator, and are, in this sense, non-specific to soot. A third category of particulate matter sensors are systems using optical scattering to determine the size and concentration of airborne particles. The optical method is too expensive for automotive applications, and secondly is subject to rapid fouling caused by soot accumulation on the optical components. The present invention differs from these approaches in a fundamental way: namely, a solid-state sensor that offers direct in situ monitoring by microwave ESR spectrometry of paramagnetic resonance signals that are characteristic of soot and other carbonaceous products of combustion.

Most diesel engine particulate emissions reduction systems are passive diesel particulate filters mounted on the engine exhaust. Soot particulates accumulate in a ceramic filter. Once the filter reaches capacity, it can be regenerated by burning off the accumulated soot. However, a different approach is to adjust the engine fuel injector timing sequence to reduce the overall quantity of soot emitted from the engine. A soot sensor, analogous to oxygen sensors used in gasoline engines, is therefore needed to implement feedback servo control of the fuel injection parameters. There are to date, however, no commercially-available vehicle mounted sensors that provide a repeatable, linear, real-time monitoring of the soot particulates generated by combustion.

This present disclosure reveals a new, low-cost, and highly specific electronic method for monitoring soot particulates in a vehicle exhaust stream. The sensor measures the electron spin resonance (also called electron paramagnetic resonance or simply paramagnetic resonance) properties of the carbonaceous products of combustion (See Literature Reference No. 1). Electron spin resonance is a microwave absorption phenomenon unique to paramagnetic substances, including several forms of carbon (See Literature Reference Nos. 2 and 3). As such, the method is sensitive and highly specific to soot.

In the present application, novel, miniaturized ESR spectrometers are disclosed for such direct sensing of soot particulates in an exhaust stream. The structure discloses a thread-in "bolt plug"-type ESR sensor suited to a high-temperature environment. This design can be mounted in a vehicle exhaust stream with minimal changes to the vehicle. Input and output channels are provided for passing the exhaust stream through the sample chamber at the center of the sensor. The present invention is robust to vibrations and fouling.

Prior related applications include U.S. application Ser. No. 11/590,522, filed Oct. 31, 2006, entitled "Method Of And Apparatus For In-Situ Measurement of Degradation of Automotive Fluids And The Like By Micro-Electron Spin Resonance (ESR) Spectrometry," and related Continuation in Part Application U.S. Ser. No. 11/983,393, filed Nov. 8, 2007, "Method of And Apparatus for In-Situ Measurement of Changes in Fluid Composition By Electron Spin Resonance (ESR) Spectrometry." These disclosures provide detailed background on the use of miniaturized, in-situ ESR sensors for measuring the properties of lubricating oils and other fluids. Neither the above referenced applications nor this present application, however, involves the first use of an ESR spectrometer, though they are believed to be the first adapted and described for the purpose of the specific invention—in the present application, the first miniaturized ESR sensor adapted to monitoring carbonaceous particulates during engine operation.

Paramagnetic Resonance of Soot

The paramagnetic resonance spectrum of soot particulates is well known in the scientific literature. In particular, the study by C. Yamanaka, T. Matsuda, and M. Ikeya, entitled "Electron spin resonance of particulate soot samples from automobiles to help environmental studies," published in 2005 (See Literature Reference No. 4), and an earlier study by M. M. Ross et al., "Electron Paramagnetic Resonance Spectrometry of Diesel Particulate Matter," published in 1982 (See Literature Reference No. 7), are directly relevant to the present invention. These articles show examples of the electron spin resonance spectrum of diesel particulate emissions. The diesel particulate spectrum has two components: a broad resonance line at g=2.1 with a line width of 80-120 mT, and a narrow resonance signal at g=2.003 with a line width of 0.4 mT (See Literature Reference No. 4). These two ESR signals respond in distinct fashion to atmospheric pressure and heat treatment (See Literature Reference No. 4 and 6). The mechanisms for the changes in the ESR spectra under vacuum, and after heat treatment, are further elucidated in *Carbon*, Volume 37, 1741-1747, (1999) (See Literature Reference No. 12), a detailed study of commercially available carbon black samples. High purity carbon black is also characterized by a broad and a narrow ESR signal. Additional examples of electron spin resonance studies of related carbon materials are given in articles references in Literature Reference Nos. 2 through 13, which incorporated herein by reference.

Prior ESR Spectrometers in General

Microwave electron spin resonance spectrometers of a myriad of types have heretofore been developed for uses other than that of the present invention. U.S. Pat. No. 4,803,624 issued Feb. 7, 1989, for example, discloses an electron spin resonance spectrometer operating at frequencies in the range of 2 to 3 GHz, using loop-gap resonators at these frequencies in a preferred embodiment. This spectrometer uses a circulator to measure the reflected microwave power from the resonator, the same as in most commercially available electron spin resonance spectrometers. Microwave circuit components, for example an isolator, circulator, power dividers, variable attenuator, and directional couplers, are arranged in a microwave bridge connected by microstrip transmission lines. External components, such as the microwave source and loop-gap resonator, are connected via SMA coaxial connectors. The microwave circuit construction uses microstrip transmission line connections formed by RF circuit boards laminated onto an aluminum backplane. This patent suggests the use of Sm—Co based permanent magnets and auxiliary field sweep coils, but does not present detailed embodiments of the magnet.

Another prior art microwave electron spin resonance spectrometer is disclosed in U.S. Pat. No. 5,233,303, issued Aug. 3, 1993. The spectrometer operates in the 2 GHz frequency range, and is intended for portable use. The design similarly uses a circulator to measure reflections from the microwave resonator containing the sample, lock-in detection, and computer control. The resonator and sample chamber is a split-ring resonator formed by plating 1-5 microns of silver onto a quartz tube. The permanent magnet design consists of an open U-shaped yoke with rectangular cross-section, two opposing cylindrical permanent magnets with amorphous iron pole pieces (e.g. Metglas), and copper wound coils to provide a modulated magnetic field ramp.

U.S. Pat. No. 4,888,554 issued Dec. 19, 1989 discloses an electron spin resonance spectrometer that detects both the absorption and dispersion signals caused by magnetic resonance, by using in phase (I) and quadrature (Q) mixers. The preferred embodiment uses a microwave circulator connected to the resonant cavity; for example, a loop-gap resonator. An automatic frequency control loop (AFC) is disclosed to servo the microwave source to the cavity resonant frequency.

Other prior art electron spin resonance spectrometers for other purposes than the present invention include U.S. Pat. No. 5,142,232 issued Aug. 25, 1992, U.S. Pat. No. 5,389,878 issued Feb. 14, 1995, and U.S. Pat. No. 5,465,047 issued Nov. 7, 1995. U.S. Pat. No. 5,142,232 discloses a spectrometer design intended to provide an inexpensive ESR system with reduced weight. A permanent magnet is provided with a moveable yoke for adjustment of the magnet field. One pair of permanent magnets is attached to a stationary yoke, and a second, moveable yoke in a parallel magnetic circuit provides mechanical adjustment of the field. Carrier suppression techniques are shown in U.S. Pat. No. 5,389,878 to reduce the carrier power reflected from the resonator, which may improve spectrometer sensitivity, depending on the noise properties of the microwave source. U.S. Pat. No. 5,465,047 shows yet another ESR spectrometer, which uses frequency sweep of the microwave source and resonator, and a fixed permanent magnet. The tunable resonator described in U.S. Pat. No. 5,465,047 is a cylindrical waveguide cavity resonator with a moveable end plate for frequency adjustment. The resonator end plate is driven by a motor.

Microwave Cavities for Prior Art ESR—Structures and Usages:

Eddy-current shielding of the audio frequency modulation field is well known in the art of electron spin resonance, and typically requires special construction techniques for the cavity design. U.S. Pat. No. 5,596,276 issued Jan. 21, 1997 uses non-uniform metal thicknesses in the construction of a rectangular waveguide cavity to reduce eddy current shielding by the metal surfaces. More commonly, thin layers of electroplated metal are used to define the microwave resonator surfaces, while providing minimal shielding of audio frequency fields. An exemplary method for building a loop-gap resonator, disclosed in U.S. Pat. No. 4,435,680 issued Mar. 6, 1984, is to machine the resonator elements from MACOR® ceramic, deposit a conductive seed layer by a chemical silvering process, and electroplate silver or copper onto the seed layer to a thickness of several microns.

Several types of apparatus have been used for handling fluids in electron spin resonance experiments. Dielectric loss is of particular importance for liquid samples containing water and requires special techniques. One type of cavity adapted to aqueous samples is shown in U.S. Pat. No. 3,931,569 issued Jan. 6, 1976. Another type of cavity with a fluid handling apparatus is disclosed in U.S. application Ser. No. 10/197,236, filed Jul. 15, 2002 and another is said parent application.

The novel ESR microwave system structures of the present invention, unlike the prior art, are specifically designed for the purposes and objectives of the invention; in the present case microwave ESR cavity systems applied to direct measurement of soot in the exhaust stream of machinery.

SUMMARY OF THE INVENTION

In summary, from one of its broader methodology aspects, the invention embraces a method of using electron spin resonance spectrometry for measuring the concentration of soot and other carbonaceous particulates, as in an operating vehicle or other machinery, that includes passing a sample of exhaust gas through a resonating RF microwave cavity resonator during the application therethrough of a relatively slowly varying substantially uniform magnetic field; relatively rapidly sweeping or modulating the magnetic field correspondingly to vary the resonant magnetic susceptibility in such exhaust sample to modulate the magnetic field passing through the cavity resonator in accordance with such magnetic susceptibility variation; and measuring the resulting RF phase or amplitude modulation to derive an electron spin resonance signal that directly senses the concentration of carbon radicals in the exhaust sample resulting from incomplete combustion during operation of the vehicle. The operation of the operating vehicle or machinery can then be altered to reduce the concentration of carbon radicals in the exhaust sample.

In the context of the present novel apparatus, the invention provides a miniature electron spin resonance sensor particularly adapted for use as an flow stream spectrometer having, in combination, a high Q miniaturized microwave cavity resonator, provided with a fluid inlet and an outlet in its walls for internally passing a fluid sample through the resonator during the resonating of the cavity resonator by microwave energy in order to effect absorption or dispersion of the microwave energy in the sample, and wherein the cavity resonator is disposed in an external uniform but variable or swept magnetic field of sufficient intensity to cause magnetic resonance in the sample within the range of magnetic field sweeping.

In still a further and preferred apparatus embodiment, the cavity resonator is of re-entrant toroidal configuration sandwiched between a single permanent magnet and coil structure and a high magnetic permittivity yoke. The resonator and magnetic field-producing structure is of miniaturized stacked construction and adapted to be mounted onboard, in situ with operating machinery, such as on board a vehicle, monitoring the carbonaceous products of combustion in exhaust gases and other fluids.

Additionally, the ESR sensor system includes a casing have a top and side walls, with at least one input port and an exit port formed in the side walls. The casing is formed such that flow stream path is formed between the input port and the exit port. A resonator cavity is formed in the casing. The resonator cavity is formed in the flow stream path such that a fluid sample flowing through the flow stream path passes through the resonator cavity. A magnet assembly is attached with the casing and proximate the resonator cavity. The magnet assembly is formed to cause a change in a magnetic susceptibility of a fluid sample flowing through the resonator cavity. An electronic circuit is to generate a high-frequency probe signal in the resonator cavity. A detector is also included to detect the phase or amplitude variations of the probe signal, such that the variations can be used to detect an undesirable by-product component in the fluid sample in the flow stream path.

In yet another aspect, a frequency discriminator circuit is electrically connected with the detector.

In yet another aspect, the magnet assembly is formed to provide a variable magnetic field through the resonator cavity such that magnetic resonance causes a change in a magnetic susceptibility of the fluid sample passed through the cavity resonator. Additionally, at a given measurement frequency, the modulation of the magnetic susceptibility of the fluid sample modulates an RF frequency of the cavity resonator, wherein the RF frequency modulation of the cavity resonator is measured by the frequency discriminator circuit, which provides an electron spin resonance signal that indicates molecular changes in the fluid sample.

In another aspect, the present invention also includes a controller for tuning the RF frequency of the resonator cavity to detect a variation in cavity quality factor with frequency due to paramagnetic resonance, where the paramagnetic resonance absorption frequency is fixed due to a constant Zeeman magnetic field.

Additionally, the resonator cavity includes a bottom and top made of a dielectric material. The resonator cavity also includes an exterior surface that is polished and metal plated to form an outer surface metal layer.

In yet another aspect, the present invention further comprises an upper pole piece and a bottom pole piece straddling the resonator cavity therebetween, with the upper pole piece positioned between the magnet and the resonator cavity. A first magnetic field path is formed, with the first magnet field path travelling axially into the upper pole piece and then radially out of the upper pole piece toward the side walls, with the field path continuing up the side walls and into the top, where it flows radially inward and then axially down into the magnet to complete the first magnetic field path. A second magnetic field path is formed, with the second magnetic field path traveling axially from the magnet through the upper pole piece and the resonator cavity and into the bottom pole piece, with the field path then flowing radially outward to the sidewalls and up the sidewalls and into the top, where it flows radially inward and then axially into the magnet to complete the second magnetic field path.

Additionally, a coil is circumferentially surrounding the magnet such that as a current is applied to the coil to generate a magnetic field, the generated magnetic field interacts with the fields of the first and second magnetic field paths to slowly vary a net magnetic field that travels uniformly through the system.

In yet another aspect, the present invention further comprises a fluid sample producing process (e.g., engine with engine exhaust); an undesirable by-product component (e.g., carbon radicals or soot) in the fluid sample (e.g., exhaust) in the flow stream path; a feedback system (sensor system and/or applicable circuitry and wiring). for receiving information related to the undesirable by-product component in the fluid sample producing process and for providing the information related to the detected undesirable by-product component to a control system; and a control system (e.g., engine control unit) for using the information from the feedback system to adjust the fluid sample producing process to reduce the undesirable by-product component.

Preferred and best mode embodiments and designs are hereinafter presented in detail.

BRIEF DESCRIPTION OF THE DRAWINGS

The objects, features and advantages of the present invention will be apparent from the following detailed descriptions of the various aspects of the invention in conjunction with reference to the following drawings, where:

FIG. 2B is a close up cross section of the end of the sensor of FIG. 2A;

FIG. 15 is a 3D drawing of the soot sensor with a single wide inlet and outlet.

Figure 1:
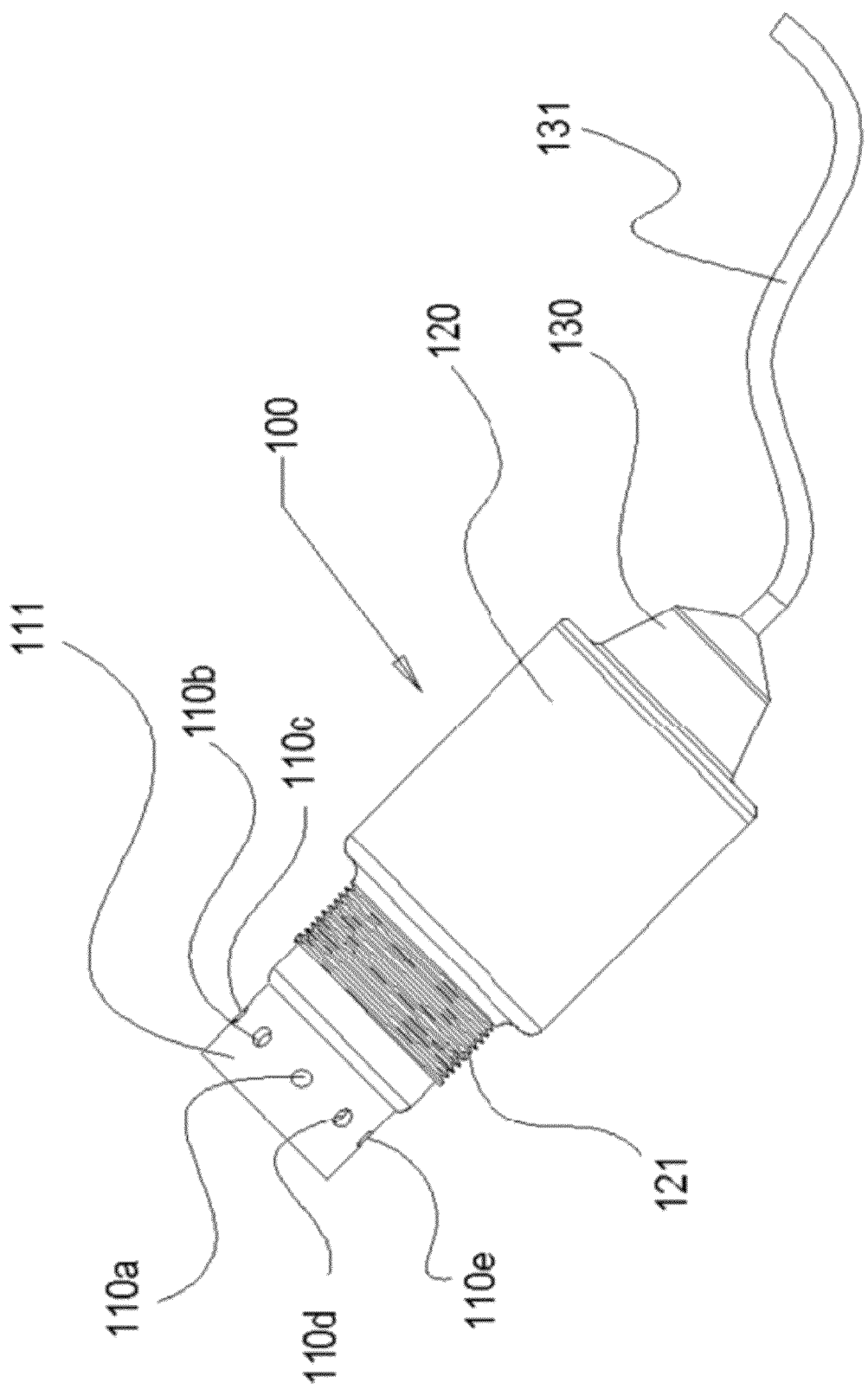
FIG. 1 is an isometric view of the present invention in its assembled miniaturized state.

In the drawings, preferred embodiments of the invention are illustrated by way of example, it being expressly understood that the description and drawings are only for the purpose of illustration and preferred designs, and are not intended as a definition of the limits of the invention.

DETAILED DESCRIPTION

The invention relates to the field of electron spin resonance (ESR) spectrometry and, more particularly, to the use of such technology for sensing the real-time, in situ emissions of soot particulates in the exhaust of operating machinery, and to a system for using the soot sensor for feedback control of the operating parameters to reduce or substantially eliminate soot emissions. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Subsequently, an introduction provides the reader with a general understanding of the present invention. Next, specific details of the present invention are provided to give an understanding of the specific aspects. Finally, a summary is provided as a synopsis of the present invention.

(1) List Of Cited Literature References

The following references are cited throughout this application. For clarity and convenience, the references are listed herein as a central resource for the reader. The following references are hereby incorporated by reference as though fully included herein. The references are cited in the application by referring to the corresponding Literature Reference No.

1. Weil, J. A., Bolton, J. R. & Wertz, J. E. Electron Paramagnetic Resonance: Elementary Theory and Practical Applications. Wiley (1994).
2. Uebersfeld, J., Etienne, A. & Combrisson, J. Paramagnetic Resonance, a New Property of Coal-like Materials. *Nature* 174, 614 (1954).
3. Pastor, R. C., Weil, J. A., Brown, T. H. & Turkevich, J. Narrow Electron Spin Resonance in Charred Dextrose. *Physical Review* 102, 918-919 (1956).
4. Yamanaka, C., Matsuda, T. & Ikeya, M. Electron Spin Resonance of Particulate Soot Samples from Automobiles to Help Environmental Studies. *Applied Radiation and Isotopes* 62, 307-311 (2005).
5. Yordanov, N. D. et al. On the Possibility for Separate Determination of Pyrolyzed Products (Soot and Polycyclic Aromatic Hydrocarbons) in Aerosols by EPR Spectrometry. *Atmospheric Environment* 35, 827-831 (2001).
6. Chugntai, A. R. et al. Adsorption and Adsorbate Interaction at Soot Particle Surfaces. *Carbon* 36, 1573-1589, (1998).
7. Ross, M. M. et al. Electron Paramagnetic Resonance Spectrometry of Diesel Particulate Matter. *Environment International* 7, 325-329, (1982).
8. Chipara, M., Lozano, K. & Chipara M. D. On the assessment of the orientation of carbon nanofibers dispersed within polyethylene by electron spin resonance. *Carbon* 45, 2692-2716 (2007).
9. Tarabek J. et al. In situ EPR spectroelectrochemistry of single-walled carbon nanotubes and C60 fullerene peapods. *Carbon* 44, 2147-2154 (2006).
10. Coleman, J. N. et al. Measurement of Nanotube Content in Pyrolytically Generated Carbon Soot. *Chem. Commun.*, 2000, 2001-2002.
11. Petit, P. et al., Electron spin resonance and microwave resistivity of single-wall carbon nanotubes. *Physical Review B* 56, 9275-9278 (1997).
12. Manivannan A., Chirila, M., Giles, N.C. & Seehra, M. S. Microstructure, dangling bonds and impurities in activated carbons. *Carbon* 37, 1741-1747 (1999).
13. Boyer, S. J. & Clarkson R. B. Electron paramagnetic resonance studies of an active carbon: the influence of preparation procedure on the oxygen response of the linewidth. *Colloids and Surfaces A: Physiochemical and Engineering Aspects.* 82, 217-224 (1994).

(2) Introduction

An object of the present invention is to provide an improved miniature electron spin resonance (ESR) sensor optimized for the in situ detection particularly, though not exclusively, of soot in an engine exhaust, and related or other machinery emissions from combustion, as indicated by the intensity of the electron spin resonance signals and variations therein to give a clear and direct indication of soot concentration. Further, the sensor responds sufficiently rapidly to changes in the intensity of the soot signals, such that the engine combustion or timing parameters can be modified to reduce the quantity of soot generated by combustion.

A further object of this invention is to provide a novel compact and robust particulate sensor free from serious vibration and environmental effects and particularly suitable for sensing the presence of free radicals in heated gases and other fluids. From the viewpoint of more specific improvements, other objects of this invention include measurement of the direct presence of free radicals using electron spin resonance wherein the magnetic circuits and resonator are provided in a highly compact, miniaturized form.

A further object is to provide a sensor that can be readily mounted into an engine, and with minimum modification to the machine, by threading the sensor into the exhaust system (e.g., pre and/or post catalytic converter). The sensor includes fluid ports to flow exhaust gas into the sample resonator, but does not require mounting of fluid fittings (using fluid fittings requires additional installation time or modification to the machinery.) A uniform but modulated magnetic field passes through the cavity, wherein the sample volume is maximized within a magnetic region of the cavity structure to increase the instrument sensitivity. The microwave resonator profile is optimized to reduce the volume of the magnetic circuit. The height of the magnet air gap (containing the resonator) is minimized in order to reduced the size of the magnet needed to achieve a given field uniformity.

Other and further objects will be explained hereinafter and are more particularly delineated in the appended claims.

(3) Specific Details

Figure 2A:
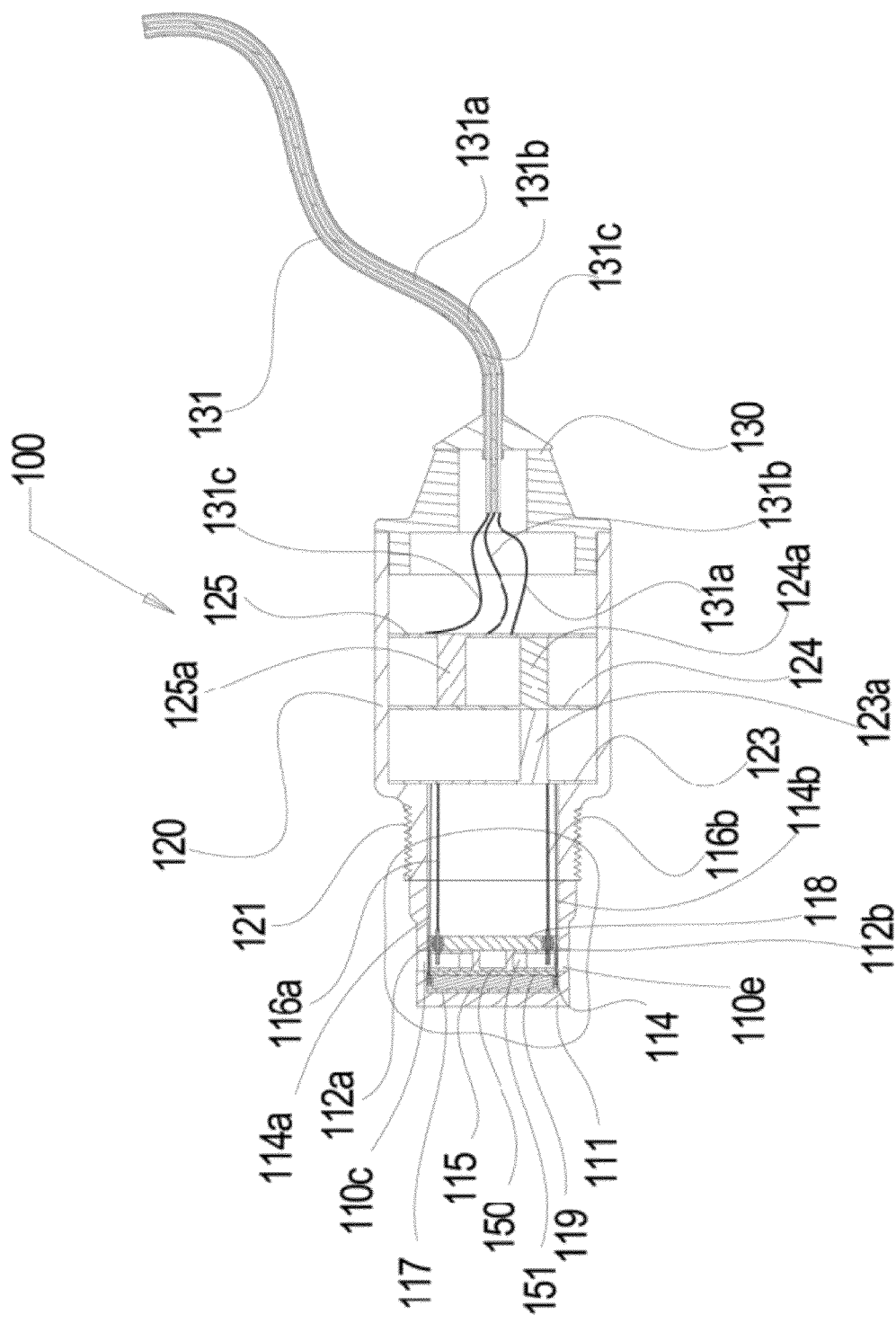
FIG. 2A is a cross section view of the present invention in its assembled miniaturized state.

FIGS. 1, 2A, and 2B show the electron spin resonance (ESR) soot sensor 100 of this invention, with its encasing structures (i.e., cylindrical sides 120 and top cap 111) with a bottom 130. As shown in FIG. 2A, the top 111 has attached to it, for example by bonding, a non-magnetic shim such as a brass shim 117, to which is then bonded axially poled cylindrical magnet 115, and the upper pole piece 119. Coil 114 with leads 114a and 114b, circumferentially surrounds the magnet 115. As current is applied to the coil 114, the generated magnetic field interacts with the field of the permanent magnet to slowly vary the net magnetic field that travels uniformly through the system.

The first magnetic field path 410 (shown in the dash-line left-side loop in FIG. 2B) travels axially into the upper pole piece 119 and then radially out to the perimeter sides 111a of the upper pole piece 119. The field lines cross the gap 333 and cross into the step feature 118c (of FIG. 2A) of the pole piece 119 (gap 333 is meant to indicate a gap between the upper pole piece 119 and the side wall (i.e., perimeter 111a). This small overlap region causes the field to saturate inside the metal before it continues up the sides 111a and into the top 111 where it flows radially inward and then axially down into the magnet 115 to complete the first magnetic circuit 410.

A second magnetic circuit 420 (shown as a dash-line right-side loop in FIG. 2B) is formed as flux flows from the permanent magnet 115 through the upper pole piece 119, across the air gap region 334 where it also passes through the resonator cavity 150 which contains the fluid sample cavity 151, and through the bottom pole piece 118. The field passes axially into the bottom pole piece 118 and the flux then flows radially outward to the sidewalls 111a and then up the sidewalls 111a and into the top plate 111 where it flows radially inward and then axially, through the non-magnetic shim 117 into the permanent magnet 115 to complete the second magnetic circuit.

It is known in the art of magnetic circuits that secondary fields (e.g., shunting magnets) can also be used to shape another field. In the present invention, however, the shunting effect is accomplished without having to use additional magnets which would have to otherwise be tuned to the primary magnet, by instead using the first saturated magnetic circuit 410 to smooth out the field lines at the outer perimeter of the pole piece, which thus reduces fringing, with the result that the second, or primary magnetic circuit 420 used in the actual ESR detection, is made very uniform, in turn making the instrument very sensitive. If the field 420 were not very uniform, magnetic resonance would be difficult to detect.

Fluid to be sensed for presence of impurities, such as the before-described free radicals, flows in and out of the cavity resonator 150; but in the present structure enters the system through, for example, input ports 110a, 110b, and 110c (shown in FIG. 1, and flows (via a flow stream path 180, shown in FIG. 2B) directly into the fluid chamber 151 of the RF microwave cavity resonator 150. The fluid then flows out of the cavity radially to an exit port, for example 110d, 110e (shown in FIG. 1). Although not shown, it can be appreciated by one skilled in the art that if there are three input ports 111a, 110b, and 110c, then there can be three corresponding exit ports 110d, 110e, and another non-illustrated exit port. The input and exit ports are located in the outer wall 111a of the casing 111 and opposite each other so as minimally to disrupt the return path of the magnetic circuit 420, thus helping to maintain its uniformity. Although round holes are shown here, other shapes, such as oblong holes can also be used, the key being to create a minimally disrupted magnetic field while allowing the fluid to be sensed to pass through without clogging. Furthermore, as shown in FIG. 15, the input and exit ports can be formed as a single entry and exit channel, or any other configuration that provides a flow stream path 180. Additionally, small electrical vias 112a and 112b may be formed in the outer periphery of the lower pole piece 118 which provide electrical connections between the resonant cavity 150 and the RF circuit board 123 (shown in FIG. 2A).

The sensor shown in FIG. 2A may be mounted into a tapped hole by means of thread 121. Controller circuit board 124, connected to RF circuit board 123 by means of connector 123a, provides analog-to-digital conversion of the demodulated sensor output signal. Power supply circuit board 125, connected to the controller board 124 by board-to-board connectors 124a and 125a provides a filtered voltage supply to power the analog-to-digital converter electronics and a variable current supply to vary the current in the coil 114. Interface wires 131a, 131b, and 131c provide power, and signal output via the shielded wire bundle 131. 130 is an environmentally shielded strain relief housing that couples the wire 131 to the housing 120.

Figure 3:
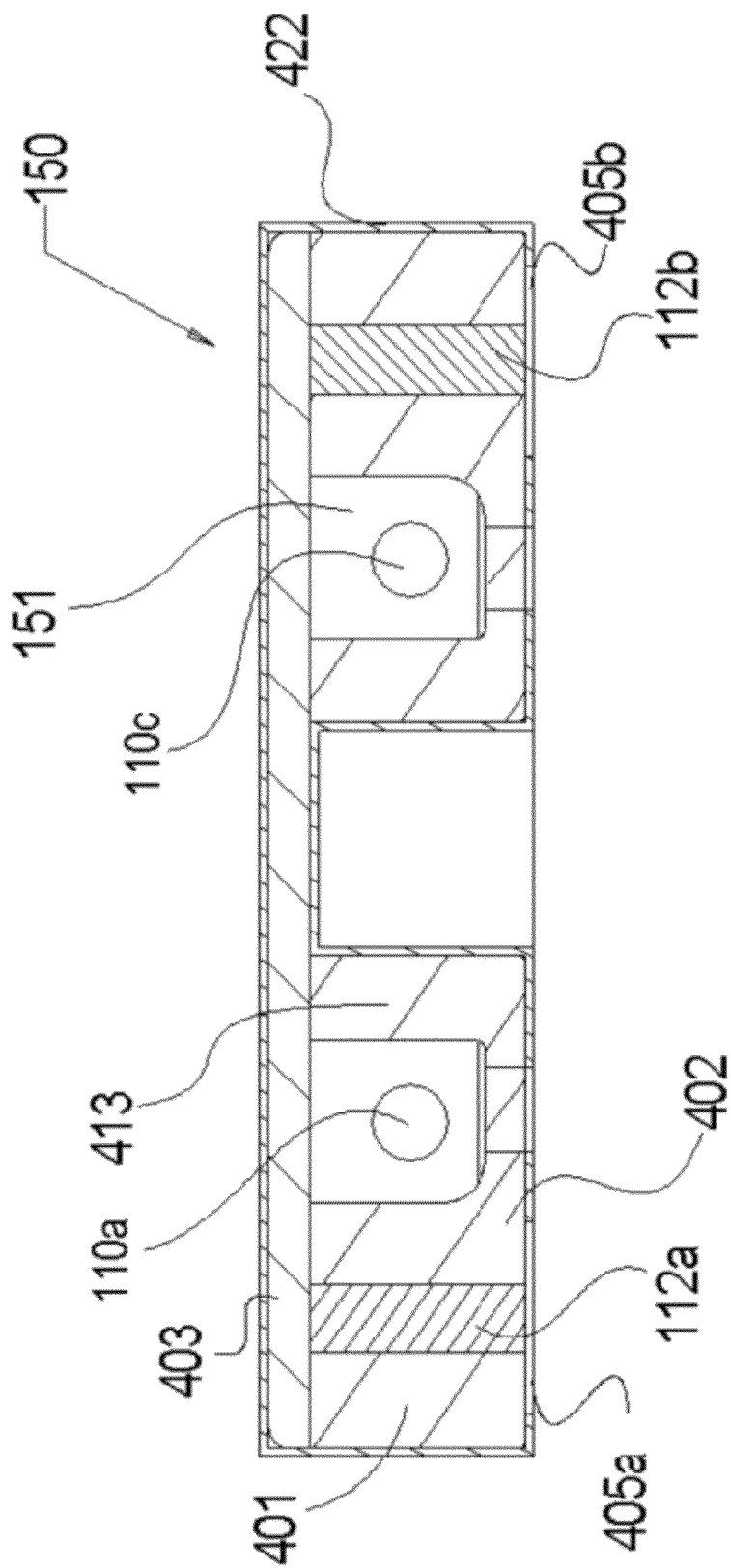
FIG. 3 is a cross section view of the toroidal resonant cavity of the present invention.

FIG. 3 presents a cross-section drawing of the RF cavity 150 showing more particularly its internal toroidal space 151. The cavity of this application may be made from two pieces of dielectric material, as shown in the hatched cross section of this substantially circularly symmetric element. Top plate 403 is bonded, for example, using a glass frit bonding process, to cylindrical sidewalls 401 which are integrally formed with bottom plate 402. A central hollow cylindrical post 413 is also integrally formed with the bottom plate 402, and the top of the post is also bonded to the bottom of top plate 403. The entire outside surface is preferably polished, e.g., by tumbling, and then it is metallized with metal layer 422, as shown in FIG. 3.

The exterior surface of the resonator 150 is preferably polished prior to metallization to reduce microwave losses caused by the skin-effect. In one embodiment, a high conductivity layer 422 is deposited on the preferably alumina surfaces using thin film metallization processes well known in the art of microwave thin film circuit fabrication. In such a typical process, a sputtered adhesion layer such as TiWi/Au is used, followed by electroplating of gold or copper. Another common metallization layer stack is Ti/NiV/Au, where the Ti layer has strong adhesion to alumina, and the NiV layer acts as a barrier layer to prevent interdiffusion of Ti and Au during soldering. High conductivity metals (e.g. gold, copper, or silver) are preferably electroplated onto the sputtered seed layer to a thickness of several times the skin depth (e.g. 4-5 microns for a resonator at 3 GHz), resulting in a metal film with low microwave loss. In a preferred embodiment, due to lower costs and improved electrical and mechanical performance, thick film metallization processes are employed to create the outer metal film 422, although the microwave performance is strongly dependent on the process used, (see, for examples, U.S. Pat. No. 5,744,232 issued Apr. 28, 1998, entitled "Low-Loss, Thick-Film Metallizations for Multilayer Microwave Packaging.")

The key features of the microwave resonator cavity 150 of the present invention are the thin walls 401 and bottom 402 and top 403 made from a dielectric such as a ceramic-like aluminum oxide, a Cerium dioxide and alumina mix known to act as a catalyst for oxidation of soot, or a glass. The exterior of the structure may be precision polished to minimize skin effect losses at high frequency and then it is metal plated to form outer surface metal layer 422. This is done with a thick film metallization process that uses one or more layers of pure, fine-grained silver paint that are fired in successive layers until a sufficient thickness is built up. The inside surface of the toroidal region 151 can be as-fired ceramic as surface finish on the interior, unplated surfaces is not as important. A capacitor is thus formed between the top and bottom surfaces of the top plate in the vicinity of the central hollow post 413.

Conductive posts 112a and 112b may be placed in the side walls 401 of the chamber opposite each other, and they couple RF energy into and out of the cavity. The base of the cavity is unplated over a circular diameter of approximately 2 to 3 mm surrounding each conductive post, shown as 405a and 405b in FIG. 3. RF energy is capacitively coupled from each conductive post to excite the cavity resonance.

The entire assembly is bonded onto the bottom pole piece 118, FIG. 2A. The posts 112a and 112b are soldered feed thrus on the bottom pole piece 118. RF power is coupled into and out of the resonator by coaxial lines 116a and 116b. Thus, the sensing region, which is exposed to high temperature gases, is isolated from the temperature-sensitive RF circuitry contained on circuit board 123.

Figure 4:
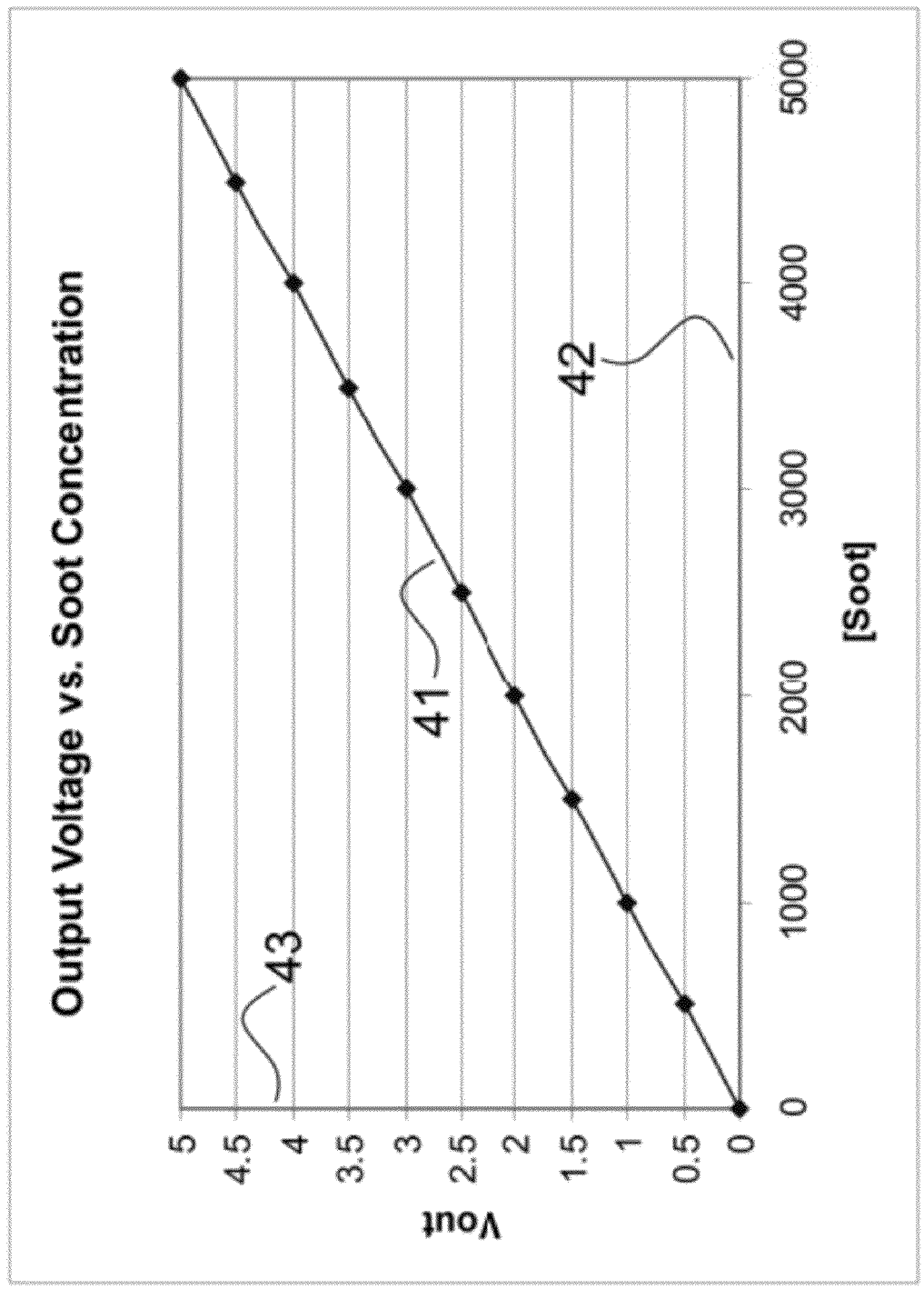
FIG. 4 is an exemplary chart of the sensor output voltage vs. soot concentration.

FIG. 4 shows a typical sensor output voltage as a function of soot concentration. The sensor output voltage 43 varies linearly with soot concentration 42, for example from 0 ppm to 5000 ppm although any range of soot concentrations can be specified by the sensor designer. The relationship between output voltage and soot concentration, 41, is linear up to the saturation of the amplifier used to magnify the output signal from the resonant cavity and frequency discriminator circuit.

Figure 5:
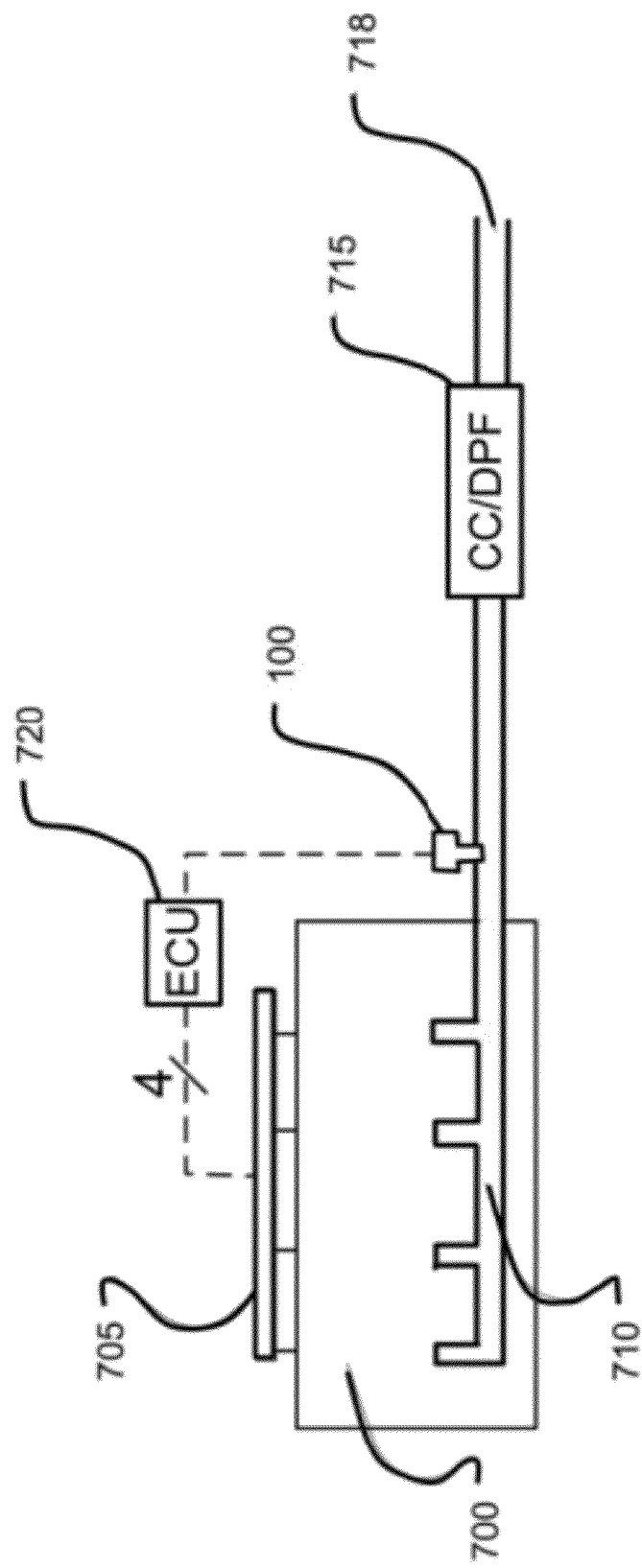
FIG. 5 is a block diagram of the engine control feedback loop with the sensor mounted at the end of the engine manifold.

FIG. 5 shows a block diagram of a feedback control loop whereby an engine 700 has an engine control unit (ECU) 720, a set of fuel injectors 705, controlled by the ECU 720, an exhaust manifold 710, a catalytic converter and/or diesel particulate filter 715 and an exhaust pipe 718. The soot concentration is measured by the sensor 100 mounted downstream of the manifold but in advance of the catalytic converter/diesel particulate filter 715, and the sensor output signal is communicated to the ECU 720 by means of a wire. The ECU then responds to the sensor output signal by adjusting the fuel injector (705) timing to minimize soot emissions.

Figure 6:
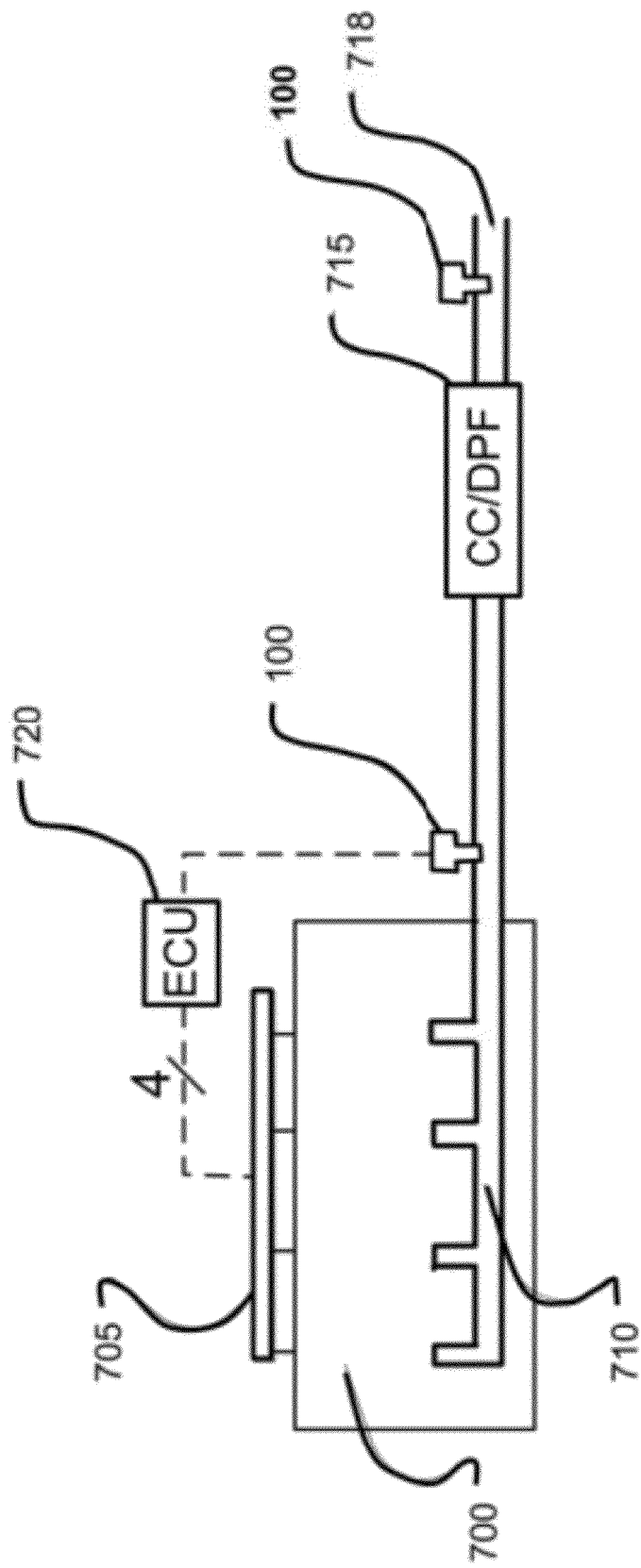
FIG. 6 is a block diagram of the sensor configured to monitor soot exhaust at the end of the tailpipe.

FIG. 6 includes the components illustrated in FIG. 5 and further shows a second soot sensor 100 mounted following the catalytic converter/diesel particulate filter 715 in order to monitor the particulate emissions from the machinery.

Figure 7:
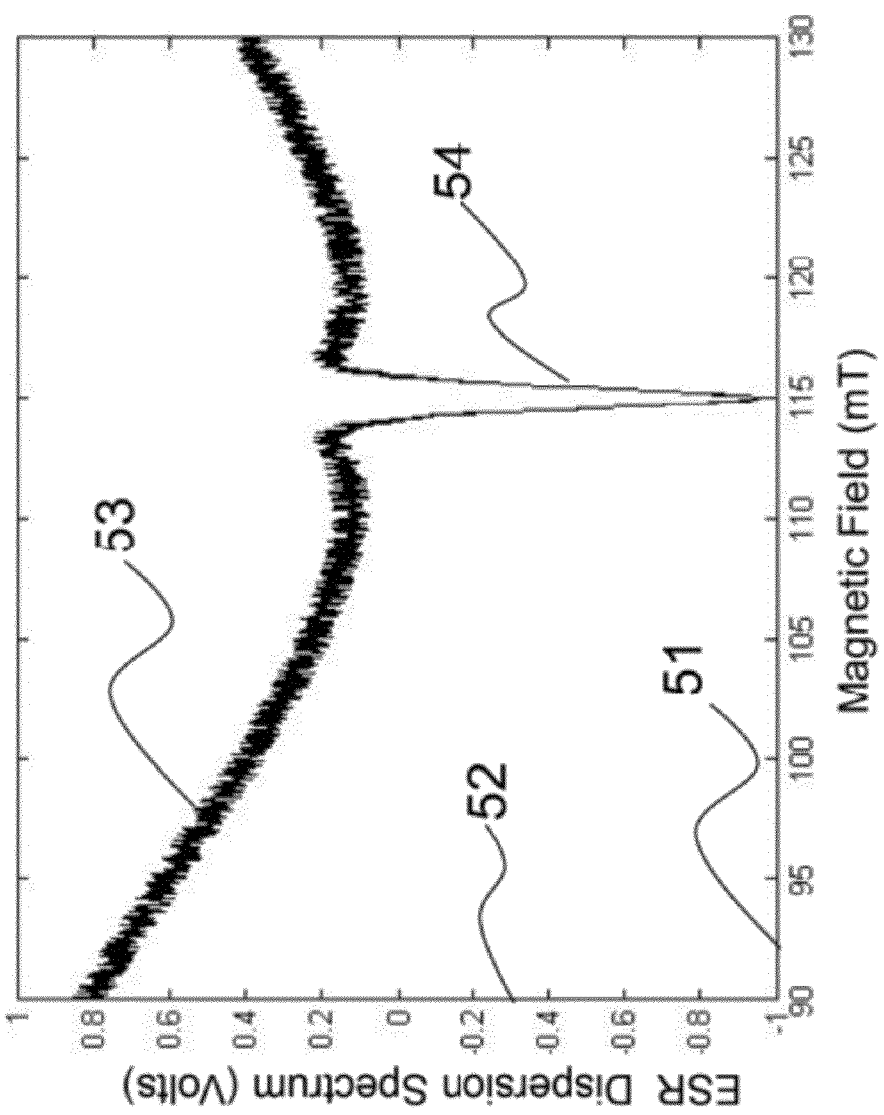
FIG. 7 is an exemplary ESR spectrum of soot.

An exemplary ESR spectrum of soot is shown in FIG. 7. The intensity 52 of the ESR spectrum varies with the magnetic field 51. A broad signal 53 is observed at g=2.1, and a narrow signal 54 is observed at g=2.003. It is known in the art that the intensity of the broad signal 53 is largely temperature-invariant while the intensity of the narrow signal 54 varies strongly with both temperature and partial-pressure of oxygen. Therefore, a preferred embodiment of the sensor 100 would be tuned to measure only the temperature-invariant signal 53 located at g=2.1.

Figure 9:
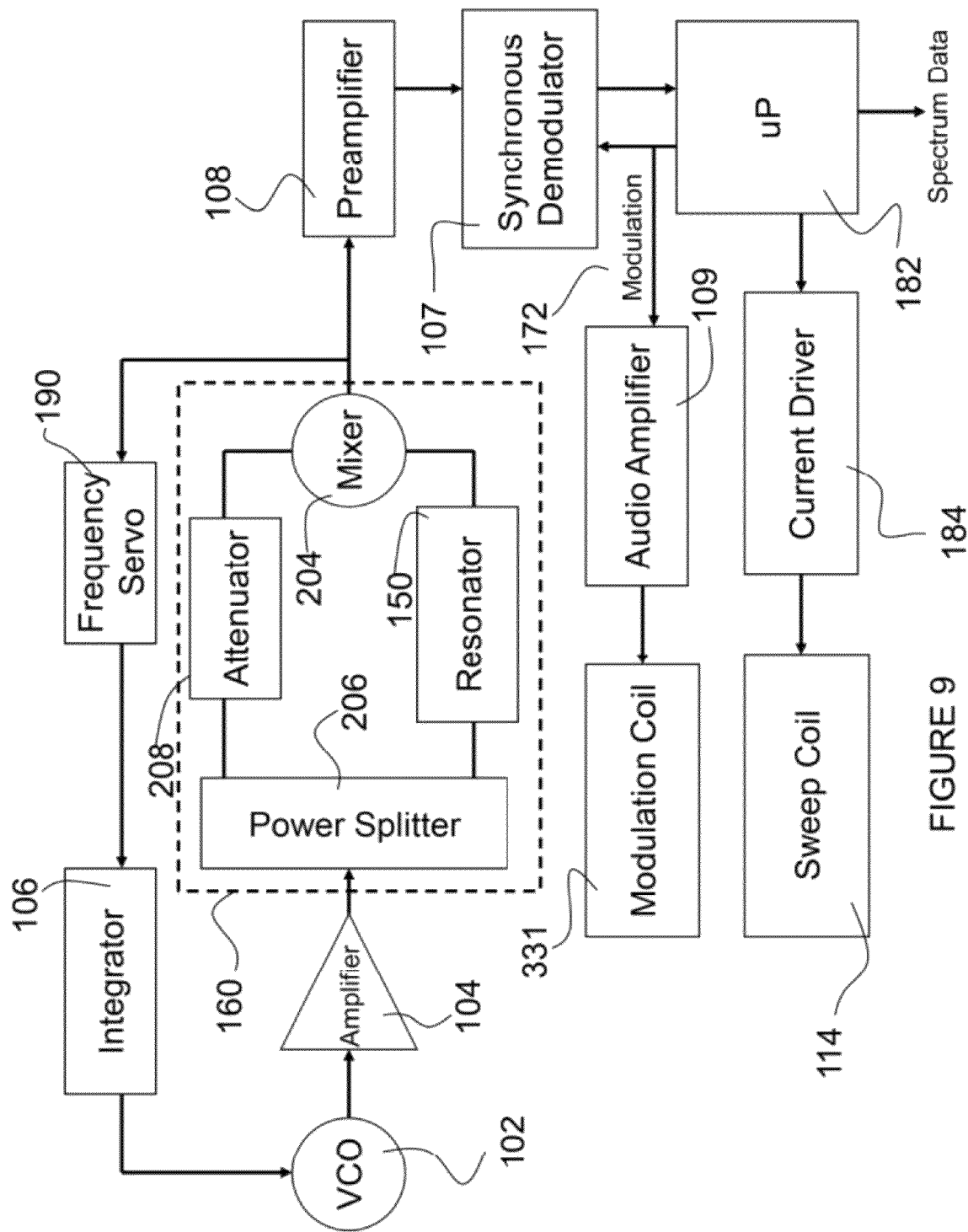
FIG. 9 is a block diagram of the complete sensor system.

FIG. 9 shows an electrical diagram of the electron spin resonance spectrometer of the present invention. The electronic circuit includes the voltage controlled oscillator (VCO) 102 that generates an RF signal which is amplified by a low noise RF amplifier 104 (to create a high-frequency probe signal). The amplifier 104 additionally provides isolation between the VCO and reflections from the power splitter 206. The frequency discriminator circuit 160 is comprised of a power splitter 206, resonator 150, the reference arm attenuator 208, and a mixer 204. The attenuator 208 sets the RF power from the power splitter 206 to the proper local oscillator (LO) drive level at the mixer 204. The mixer 204 is configured as a phase detector; that is, the LO signal from the attenuator 208 has a 90° phase difference at the cavity resonant frequency from the signal coupled through the resonator 150 to RF input of the mixer input. In operation, magnetic resonance induces phase variations of the signal coupled through the resonator 150 due to variations in the magnetic susceptibility of the sample; these phase variations are demodulated by the frequency discriminator circuit.

The audio-frequency components of the spectrometer shown in FIG. 9 are a preamplifier 108, synchronous detector 107 (e.g., demodulator), audio amplifier 109, and modulation coil 331. Modulation waveforms 172 are generated by a microprocessor 182 (or external A/D converters, not shown) to drive the modulation coil 331 and provide a reference signal to the synchronous demodulator 107. The rapid modulation coil 331 varies the magnetic field at the sample at an audio frequency, for example, 6 kHz. The rapidly modulated field is superimposed on the slowly varying magnetic field, thereby eliminating the need for two separate coils as was the case in the prior art. The corresponding changes in the magnetic susceptibility of the sample due to magnetic resonance cause variations in the resonant frequency of the resonator 150, which in turn induce phase modulation sidebands on the RF carrier coupled through the resonator. The phase variations are demodulated by the frequency discriminator circuit, then detected using the preamplifier 108 and synchronous detector 107.

The field sweep coil 114 (shown schematically in FIG. 9 and in its place in the sensor in FIG. 2A) is used to slowly vary the uniform magnetic field at the sample, via a current driver 184, also controlled by the microprocessor 182. The current driver may generate currents of several amps, for example 2.2 A. In a preferred embodiment, the current driver generates both positive and negative currents, enabling the user to precisely either increase or decrease the uniform field 420 in region 334 of FIG. 2B.

For the purpose of illustrating this preferred embodiment of the present invention, examples of the RF circuit components used in the frequency discriminator 160 are a surface mount double balanced mixer 204 such as Mini-Circuits Inc. (Brooklyn, N.Y.) model SIM-43+, a surface mount 3 dB attenuator such as Mini-Circuits Inc. model GAT-3+, and a surface mount 0° RF power splitter 206 such as Mini-Circuits Inc. model SP-2L+.

The phase noise of the VCO 102 is one of the determining factors of the spectrometer sensitivity. In this embodiment of the invention a low-phase noise, low-vibration sensitivity, surface mounted voltage-controlled oscillator is used, such as model CRO3170C-LF from Z-Communications, Inc. (San Diego, Calif.) and model DCRO307331-10 from Synergy Microwave Corporation (Paterson, N.J.). A second VCO, such as model CRO3170C-LF is a coaxial resonator based oscillator with a tuning range of 3070-3270 MHz and a phase noise of −108 dBc/Hz @ 10 kHz offset, according to the manufacturer specifications. A second preferred VCO model DCRO307331-10, is based on use of stripline resonators, which may have reduced vibration sensitivity compared to coaxial resonators, and is tunable from 3075 to 3310 MHz, being swept in the parent application, but fixed in the present invention improvement. The phase noise specification for model DCRO307331-10 is −100 dBc/Hz @ 10 kHz offset.

Figure 8:
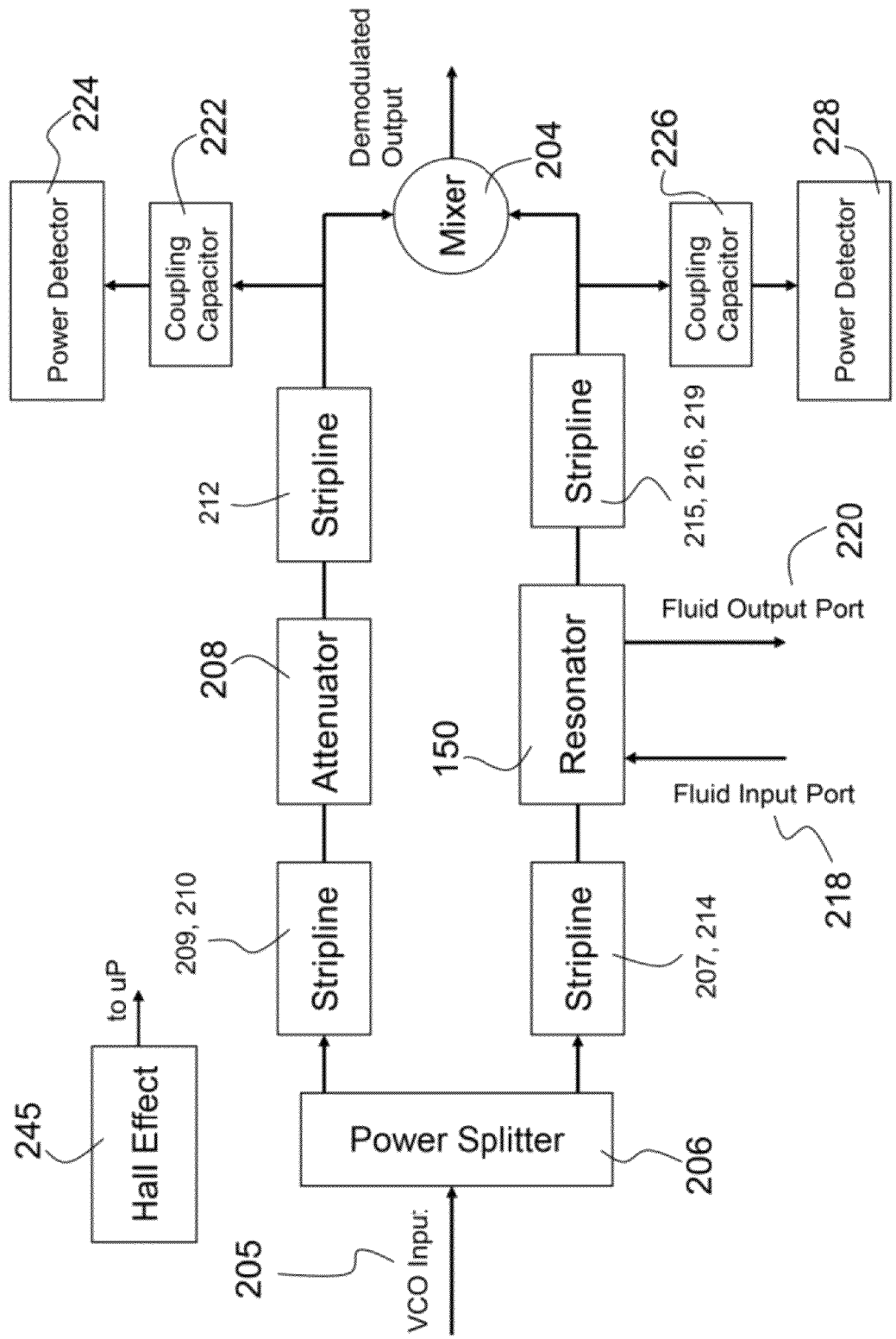
FIG. 8 is a block diagram of the major electronic components of the soot sensor.

Additional components shown in FIG. 8 are RF power detectors 224 and 228. Relative changes in the RF power at the resonator output indicate changes in the resonator insertion loss, for example, due to dielectric loss in the fluid sample. The preferred embodiment of the present invention uses low-cost RF power detectors such as model LTC5508 from Linear Technology, Inc. (Milpitas, Calif.). Coupling capacitors 222 and 226 are used to tap a small amount of RF power at each mixer input for monitoring by the power detectors. The RF power coupled to the detector is on the order of −10 dB or −15 dB; the majority of the power is coupled to the mixer. The coupling element may be a directional coupler or a lumped circuit. Simple capacitor coupling circuits are described in Linear Technology Application Note 91 (October 2002), entitled "Low Cost Coupling Methods for RF Power Detectors Replace Directional Couplers." High accuracy, small value RF tapping capacitors are available from suppliers such as American Technical Ceramics (Huntington Station, N.Y.), for example, part number 600L0R3BT or similar. In FIG. 8, RF coupling capacitors such as 222 and 226 are high-Q RF capacitors chosen for best insertion loss performance in the 3-3.5 GHz range, such as part number 600L2R0BT.

The aforementioned examples of circuit components are merely indicative of a preferred embodiment of the invention. A spectrometer design using different component models, as well as variations in the spectrometer circuits, can be readily devised by a person skilled in the art of RF and microwave circuit design given the description herein.

Turning again to FIG. 9, a frequency servo loop 190 integrates the discriminator output from the mixer using integrator 106 and locks the frequency of the VCO 102 to the frequency of the miniaturized resonator 150 shown in FIG. 3 (through which the fluid being sensed is flowing). The bandwidth of the VCO frequency servo is slow compared to the audio modulation frequency of the modulation 172. An example of the audio modulation frequency as before stated may be 6 kHz, while the loop bandwidth of the servo 190 may be less than 1 kHz. The VCO tracks the relatively slow frequency changes of the resonator 150, which may be frequency changes caused by thermal drift, but does not follow the relatively rapid audio frequency modulation of the resonator frequency caused by magnetic resonance of the sample. In contrast to many embodiments of ESR spectrometers found in the prior art, with the present invention, there is no requirement for user adjustment of the VCO frequency or any elements of the microwave bridge. This is, in part, because of the frequency discriminator circuit 160 uses a 2-port transmission coupled resonator 150, rather than the conventional reflection based design using a circulator. In more detail, the electrical lengths of the frequency discriminator transmission lines are carefully simulated to obtain the correct phase relationships at the mixer 204, and similarly, the resonator 150 is carefully simulated to obtain an accurate s-parameter model. With the use of accurate modeling, no user adjustment to the frequency discriminator elements is required for proper operation and resonator coupling. The circuit design shown here is also advantageous in that the frequency discriminator components are integrated in close proximity inside the magnet housing, in contrast to prior art where the microwave bridge is external to the magnet. In particular, a circulator has a magnetic housing of its own which would distort the magnetic field inside the spectrometer magnet. Further, the resonator is mounted in close proximity to the same board as the frequency discriminator, which has the advantage that the transmission line connections between the circuit elements are electrically short. Again, this is in contrast to prior art spectrometers, which use waveguide or coaxial connections to the cavity resonator with relatively long sections of transmission line cable (or waveguide) connecting to the microwave bridge.

As shown in greater detail in FIG. 8, the frequency discriminator subsystem is shown integrated onto RF PCB board 123 using stripline, microstrip and/or coaxial transmission lines 207, 209, 210, 212, 214, 215, 216 and 219. In order for the mixer to operate as a phase detector, the two RF signal paths must converge in quadrature (90 degrees out of phase). It is in order to analyze the phase variation across the two separate paths to ensure correct operation. FIG. 8 shows a block diagram of the two RF paths between the power splitter 206 and the mixer 204. The top path travels through an attenuator 208, while the bottom path travels through the resonator 150. Both paths also go through various lengths of transmission line 207, 209, 210, 212, 214, 215, 216 and 219. RF coupling capacitors 222 and 226 are also used. Each of these components can be modeled to generate S-parameters, which can then be analyzed in a linear analysis tool to extract phase length variation.

One method to generate the S-parameters for the resonator 150 is to build and simulate it in a finite method element solver such as Ansoft HFSS. A similar set of data for the attenuator 208 can be obtained from the manufacturer's web site. This data can be imported into a linear analysis tool such as Genesys, and transmission line lengths can be estimated. A further step is to import the full physical layout into HFSS. This includes the resonator 150, the transmission line sections 207, 209, 210, 212, 214, 215, 216, and 219, and any vias or surface pads which can affect the phase length. Likewise, coupling capacitors 222 and 226 may be included in the model using s-parameters from the manufacturer's web site.

Figure 12:
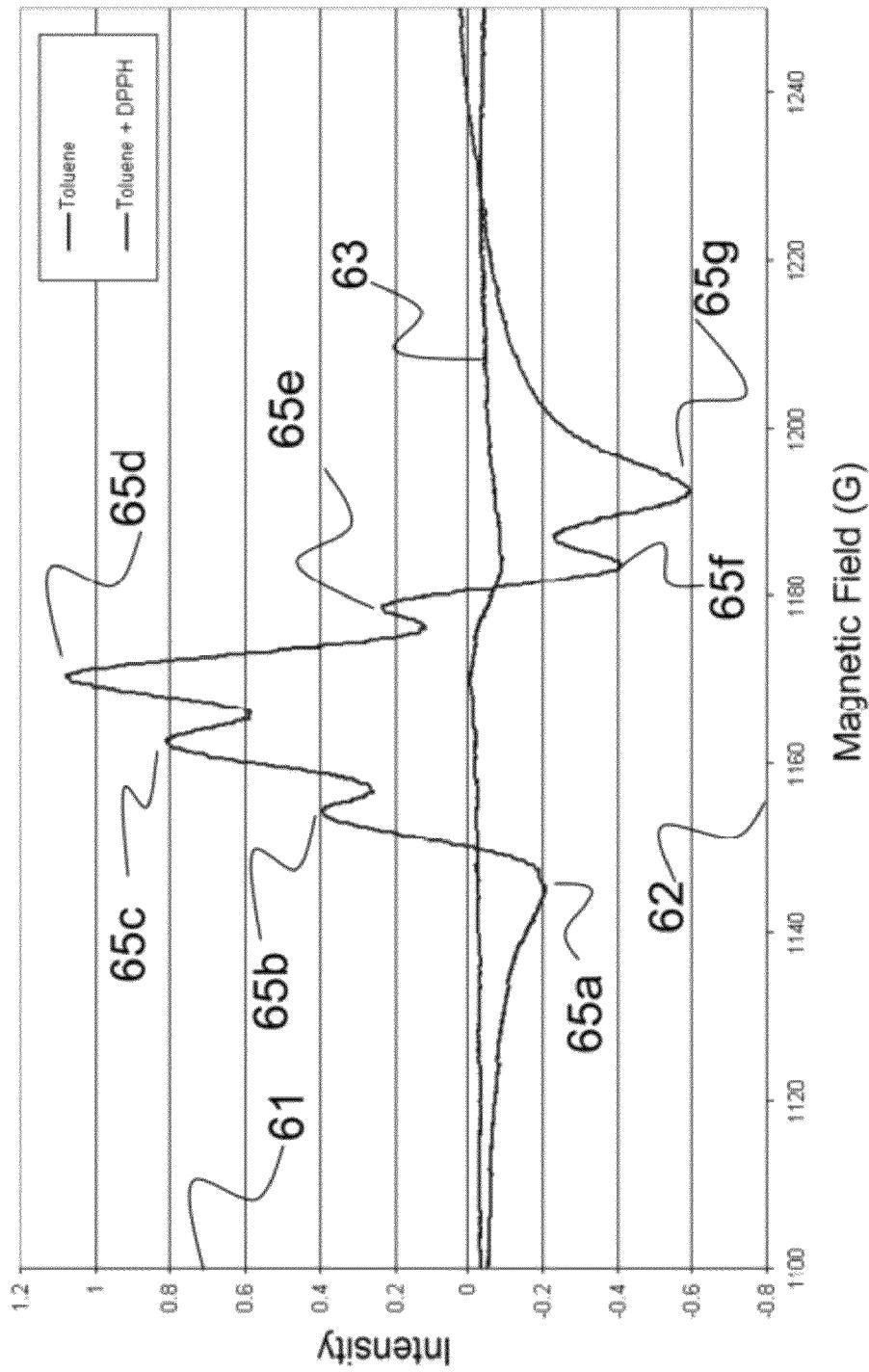
FIG. 12 shows the ESR spectrum of a sample of DPPH dissolved in toluene obtained experimentally using a miniaturized ESR sensor.

An example of the sensor output is shown in FIG. 12. The baseline ESR spectrum of the resonator 63 is plotted as a function of magnetic field 62 and signal intensity 61. There is a small resonance due to iron impurities in the alumina resonant cavity. When a sample of 0.1% by weight DPPH dissolved in toluene solvent is introduced, a characteristic spectrum 64 is observed with multiple peaks 65a, 65b, 65c, 65d, 65e, 65f, and 65g which are due to hyperfine splitting in the sample.

Figure 11:
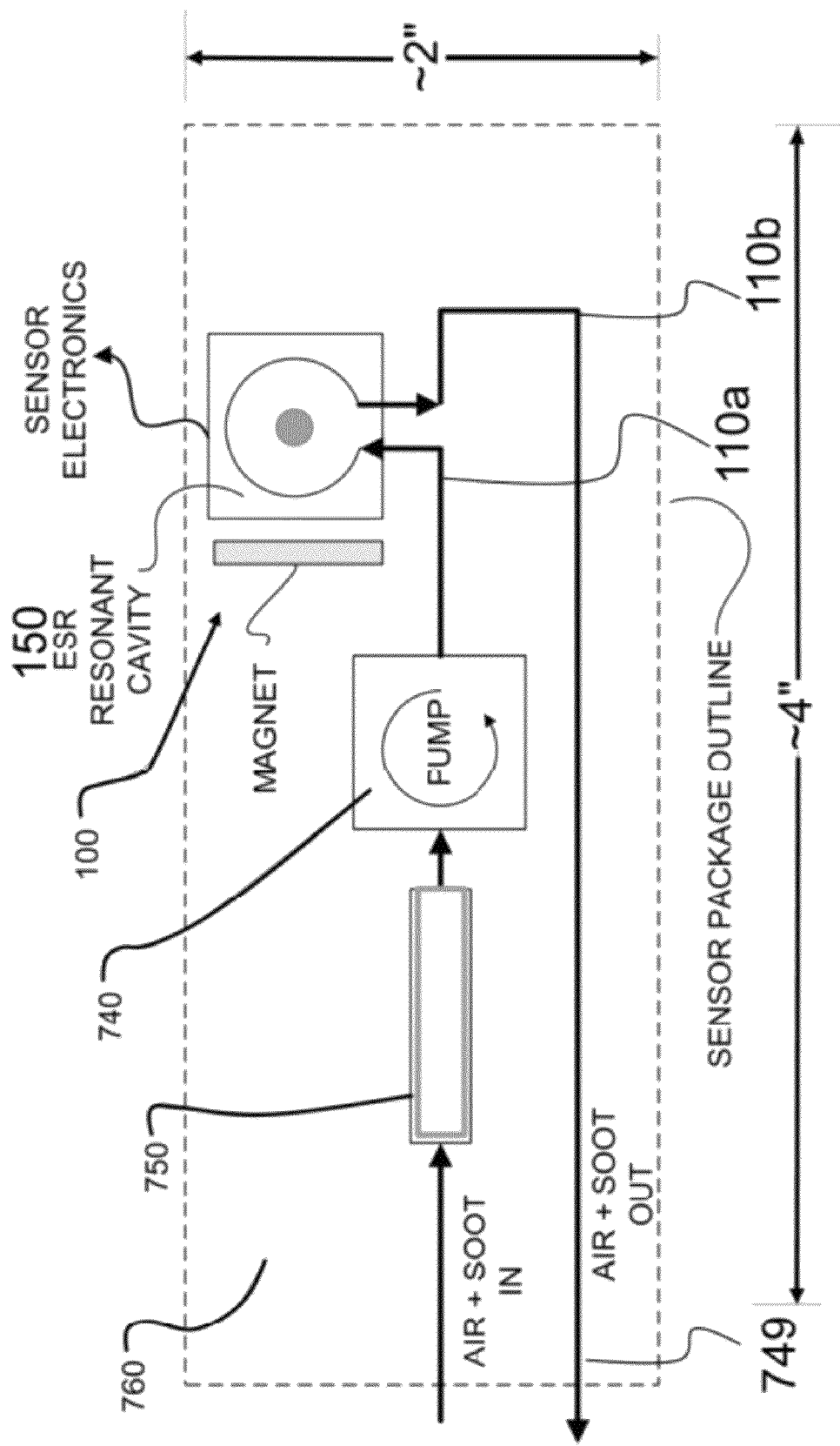
FIG. 11 is a schematic diagram of a complete, stand-alone air sampling sensor, showing the use of the soot sensor in conjunction with a vacuum pump and controller.

The installation of the sensor 100 of the invention in an exemplary standalone airborne soot measuring system is shown in FIG. 11, wherein a small pump 740 draws air from the environment at 750 ("air in"), into the inlet 110a and through the resonant cavity 150, exiting at 110b and 749 ("air out") such that a sample of the air (or other fluids (i.e., air is a fluid)) can be continuously introduced into and withdrawn from the sensor in a controlled and continuous pass-through manner. By introducing a filter material, for example porous ceramic, into the resonant cavity 150, a large fraction of the particulate matter in the sample air stream may be captured in the sensor for the purposes of increasing sensitivity. After a sample has been taken for a given time, the sensor may be regenerated by heating the filter material to oxidize the entrained soot. Although not limited thereto, the overall miniaturized sensor package of FIG. 11 may be about two and three-eighths inches in diameter and four inches tall.

Figure 10:
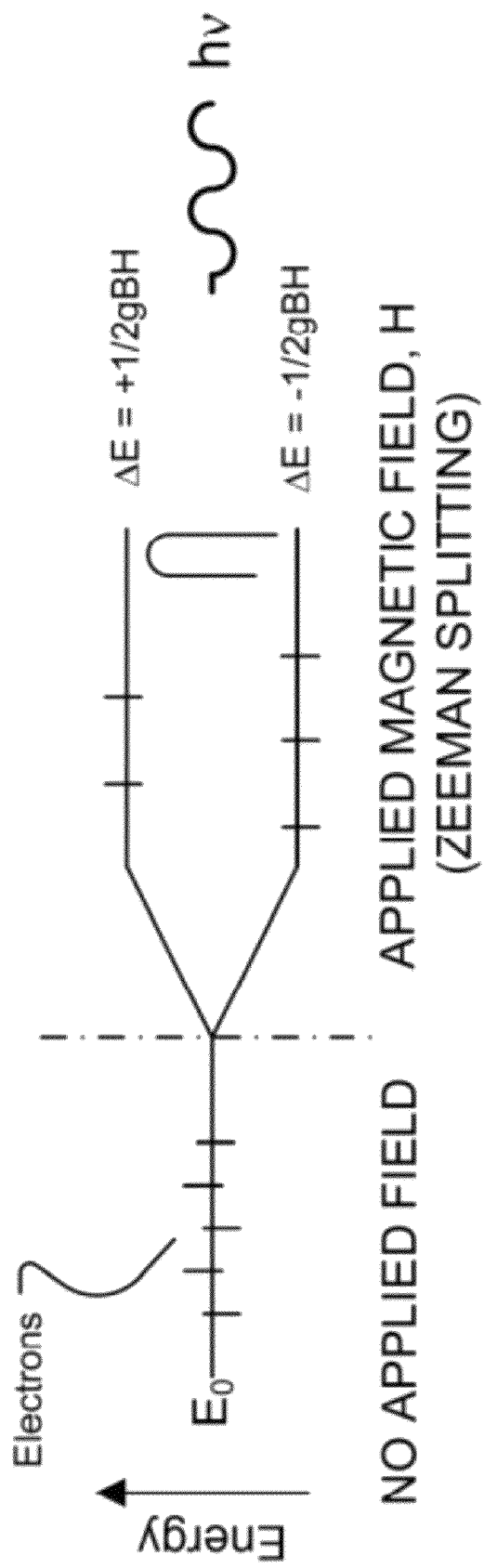
FIG. 10 is an explanatory diagram of electron energy transitions stimulated in a sample of carbon free radical under incident microwave energy and in the applied magnetic field, showing the Zeeman splitting effect under such magnetic field.

Magnetic resonance causes a change in the magnetic susceptibility of the air sample passed through the cavity resonator at a frequency depending on the Zeeman field at the fluid sample (FIG. 10). The modulation of the magnetic field applied by the modulation driver and coil 114 (~0.1-10 Gauss amplitude) varies the Zeeman field at the sample and therefore the frequency of magnetic resonance. At a given measurement frequency, the modulation of the magnetic susceptibility of the fluid sample modulates the RF frequency of the cavity resonator 150. The frequency modulation of the cavity resonator 150 is measured by the above-described frequency discriminator circuit 160. Such measurement provides an electron spin resonance signal that directly indicates the molecular changes in the fluid samples resulting from variation in the carbonaceous soot entrained in the exhaust gas during operation of the engine.

Figure 14:
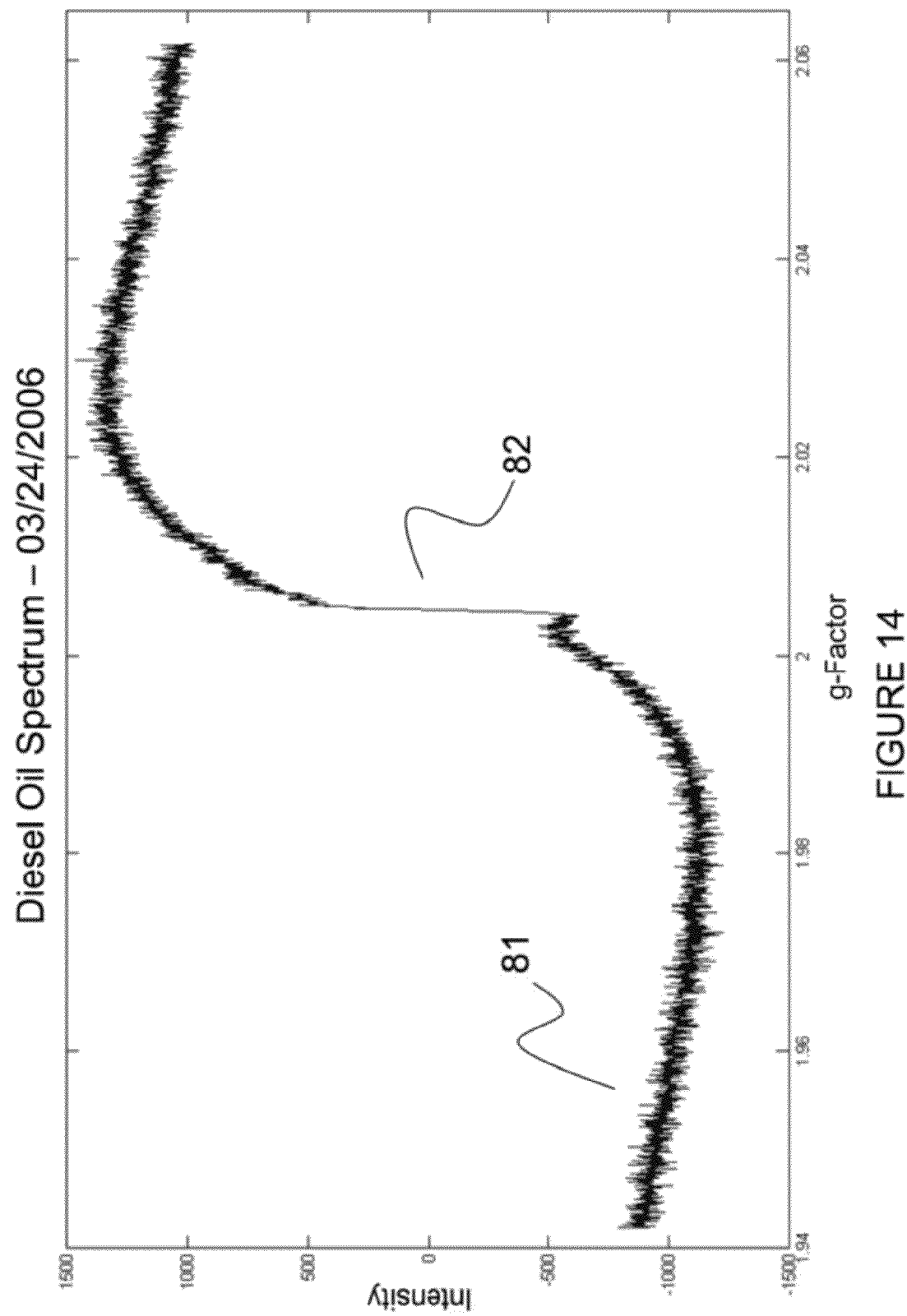
FIG. 14 shows the ESR spectrum of soot and peroxy radical in diesel engine oil, obtained experimentally using a conventional X-band ESR spectrometer.

X-band ESR measurements of used diesel oil samples, which contain a high concentration of dissolved soot are shown in FIG. 14. A peroxy radical signal 82 is the resonance at a g-factor near 2.0055. A broader signal 81 is attributed to soot.

Figure 13:
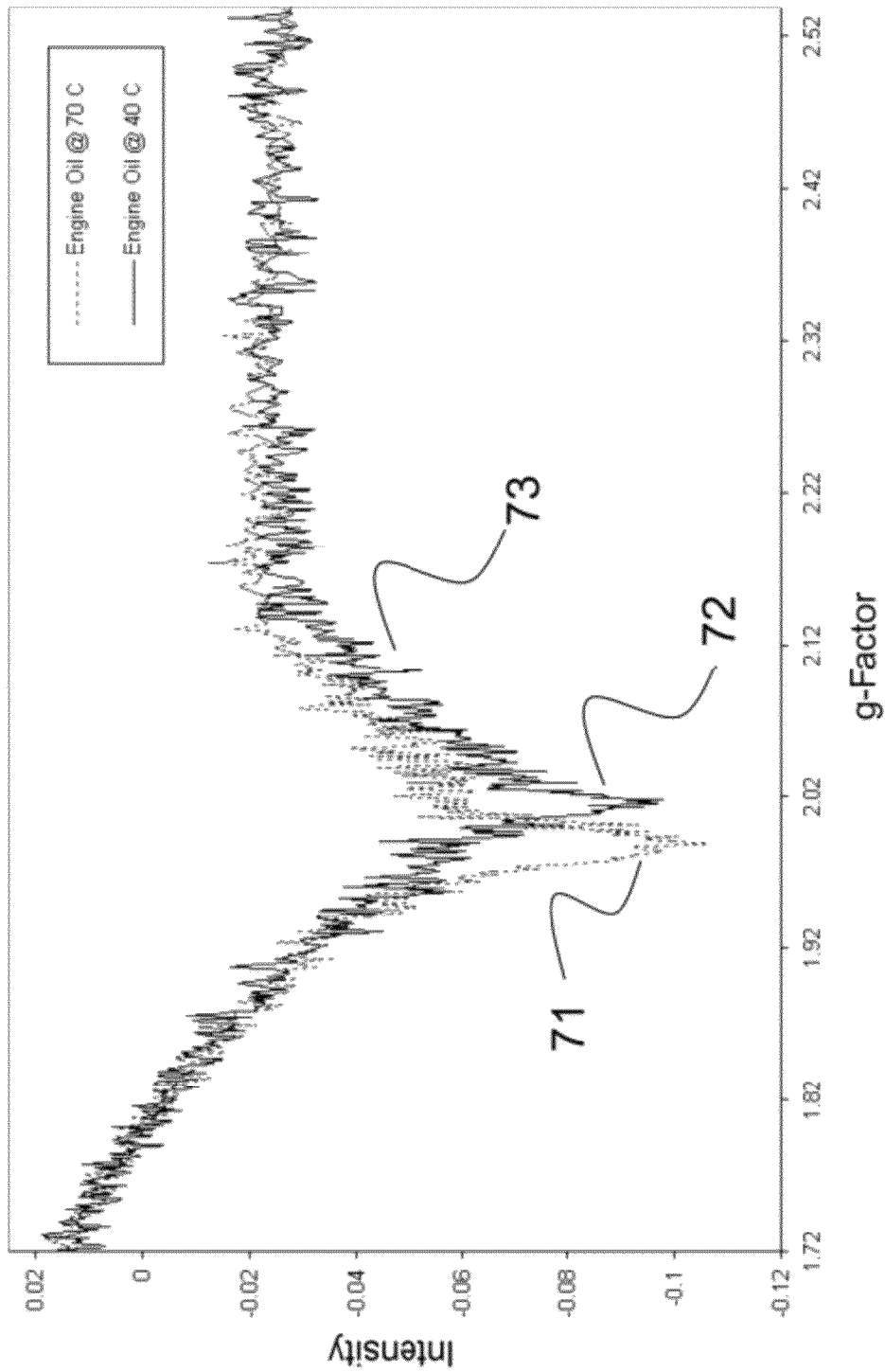
FIG. 13 shows the ESR spectrum of soot dissolved in engine oil at two different temperatures, obtained experimentally using a miniaturized ESR sensor.

A similar spectrum from the miniaturized electron spin resonance spectrometer described herein is shown in FIG. 13. Two signals, a narrow signal 71 at approximately g=2.01, and a broad signal 73 at g=2.02 are superimposed. It is interesting to note that the g-value of the narrow signal 71 varies slightly with temperature, shifting to 72, while the broad signal 73 remains substantially unchanged.

FIG. 15 shows an embodiment of the invention 500 with a single wide channel 520 through which directionalized flow (as in an exhaust pipe) 530 flows through. This shape acts to accelerate the flow through the sensor and help keep it clean. The barrel of the sensor 540 connected to cable 510 contains the interior components shown in FIG. 2A.

While the invention has been described with particular reference to the important application for in situ on-board monitoring of airborne soot concentration, the novel ESR sensor construction of the invention may also be usefully employed with other fluids and materials and in a myriad of other applications in other fields; and further modifications will therefore occur to those skilled in this art, such being considered to fall within the spirit and scope of the invention as defined in the appended claims.

(4) Summary

In summary, from one of its broader methodology aspects, the invention embraces a method of using electron spin resonance spectrometry for measuring the concentration of soot and other carbonaceous particulates, as in an operating vehicle or other machinery. The method includes passing a sample of exhaust gas through a resonating RF microwave cavity resonator during the application therethrough of a relatively slowly varying substantially uniform magnetic field. The next act includes relatively rapidly sweeping or modulating the magnetic field correspondingly to vary the resonant magnetic susceptibility in such exhaust sample to modulate the magnetic field passing through the cavity resonator in accordance with such magnetic susceptibility variation. The resulting RF phase or amplitude modulation is then measured to derive an electron spin resonance signal that directly senses the concentration of carbon radicals in the exhaust sample resulting from incomplete combustion during operation of the vehicle. The operation of the operating vehicle or machinery can then be altered to reduce the concentration of carbon radicals in the exhaust sample. As can be appreciated by one skilled in the art, the present invention includes the applicable sensor, components, and circuitry to perform the operations described above.

What is claimed is:

1. An electron-spin resonance (ESR) sensor system, comprising
    a casing have a top and side walls, with at least one input port and an exit port formed in the side walls, the casing formed such that flow stream path is formed between the input port and the exit port;
    a resonator cavity formed in the casing, the resonator cavity being formed in the flow stream path such that a fluid sample flowing through the flow stream path passes through the resonator cavity;
    a magnet assembly attached with the casing and proximate the resonator cavity, the magnet assembly being formed to cause a change in a magnetic susceptibility of a fluid sample flowing through the resonator cavity;
    an electronic circuit to generate a high-frequency probe signal in the resonator cavity; and
    a detector to detect the phase or amplitude variations of the probe signal, such that the variations can be used to detect an undesirable by-product component in the fluid sample in the flow stream path.

2. The ESR sensor system of claim 1, further comprising a frequency discriminator circuit electrically connected with the detector.

3. The ESR sensor system of claim 2, wherein the magnet assembly is formed to provide a variable magnetic field through the resonator cavity such that magnetic resonance causes a change in a magnetic susceptibility of the fluid sample passed through the cavity resonator, and wherein at a given measurement frequency, the modulation of the magnetic susceptibility of the fluid sample modulates an RF frequency of the cavity resonator, wherein the RF frequency modulation of the cavity resonator is measured by the frequency discriminator circuit, which provides an electron spin resonance signal that indicates molecular changes in the fluid sample.

4. The ESR sensor system of claim 3, further comprising a controller for tuning the RF frequency of the resonator cavity to detect a variation in cavity quality factor with frequency due to paramagnetic resonance, where the paramagnetic resonance absorption frequency is fixed due to a constant Zeeman magnetic field.

5. The ESR sensor system of claim 4, wherein the resonator cavity includes a bottom and top made of a dielectric material.

6. The ESR sensor system of claim 5, wherein the resonator cavity includes an exterior surface that is polished and metal plated to form an outer surface metal layer.

7. The ESR sensor system of claim 6, further comprising:
    an upper pole piece and a bottom pole piece straddling the resonator cavity therebetween, with the upper pole piece positioned between the magnet and the resonator cavity;
    a first magnetic field path, the first magnet field path travelling axially into the upper pole piece and then radially out of the upper pole piece toward the side walls, with the field path continuing up the side walls and into the top, where it flows radially inward and then axially down into the magnet to complete the first magnetic field path;

a second magnetic field path, the second magnetic field path traveling axially from the magnet through the upper pole piece and the resonator cavity and into the bottom pole piece, with the field path then flowing radially outward to the sidewalls and up the sidewalls and into the top, where it flows radially inward and then axially into the magnet to complete the second magnetic field path.

8. The ESR sensor system of claim 7, further comprising a coil circumferentially surrounding the magnet such that as a current is applied to the coil to generate a magnetic field, the generated magnetic field interacts with the fields of the first and second magnetic field paths to slowly vary a net magnetic field that travels uniformly through the system.

9. The ESR sensor system of claim 8, further comprising:
a fluid sample producing process;
an undesirable by-product component in the fluid sample in the flow stream path;
a feedback system for receiving information related to the undesirable by-product component in the fluid sample producing process and for providing the information related to the detected undesirable by-product component to a control system; and
a control system for using the information from the feedback system to adjust the fluid sample producing process to reduce the undesirable by-product component.

10. The ESR sensor system of claim 1, wherein the magnet assembly is formed to provide a variable magnetic field through the resonator cavity such that magnetic resonance causes a change in a magnetic susceptibility of the fluid sample passed through the cavity resonator, and wherein at a given measurement frequency, the modulation of the magnetic susceptibility of the fluid sample modulates an RF frequency of the cavity resonator, wherein the RF frequency modulation of the cavity resonator is measured by the frequency discriminator circuit, which provides an electron spin resonance signal that indicates molecular changes in the fluid sample.

11. The ESR sensor system of claim 1, further comprising a controller for tuning a frequency of the resonator cavity to detect a variation in cavity quality factor with frequency due to paramagnetic resonance, where the paramagnetic resonance absorption frequency is fixed due to a constant Zeeman magnetic field.

12. The ESR sensor system of claim 1, wherein the resonator cavity includes a bottom and top made of a dielectric material.

13. The ESR sensor system of claim 1, wherein the resonator cavity includes an exterior surface that is polished and metal plated to form an outer surface metal layer.

14. The ESR sensor system of claim 1, further comprising:
an upper pole piece and a bottom pole piece straddling the resonator cavity therebetween, with the upper pole piece positioned between the magnet and the resonator cavity;
a first magnetic field path, the first magnet field path travelling axially into the upper pole piece and then radially out of the upper pole piece toward the side walls, with the field path continuing up the side walls and into the top, where it flows radially inward and then axially down into the magnet to complete the first magnetic field path;
a second magnetic field path, the second magnetic field path traveling axially from the magnet through the upper pole piece and the resonator cavity and into the bottom pole piece, with the field path then flowing radially outward to the sidewalls and up the sidewalls and into the top, where it flows radially inward and then axially into the magnet to complete the second magnetic field path.

15. The ESR sensor system of claim 14, further comprising a coil circumferentially surrounding the magnet such that as a current is applied to the coil to generate a magnetic field, the generated magnetic field interacts with the fields of the first and second magnetic field paths to slowly vary a net magnetic field that travels uniformly through the system.

16. The ESR sensor system of claim 1, further comprising:
a fluid sample producing process;
an undesirable by-product component in the fluid sample in the flow stream path;
a feedback system for receiving information related to the undesirable by-product component in the fluid sample producing process and for providing the information related to the detected undesirable by-product component to a control system; and
a control system for using the information from the feedback system to adjust the fluid sample producing process to reduce the undesirable by-product component.

* * * * *